United States Patent
Naya et al.

(10) Patent No.: US 7,501,649 B2
(45) Date of Patent: Mar. 10, 2009

(54) SENSOR INCLUDING POROUS BODY WITH METAL PARTICLES LOADED IN THE PORES OF THE BODY AND MEASURING APPARATUS USING THE SAME

(75) Inventors: Masayuki Naya, Kaisei-machi (JP);
Atsushi Mukai, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 74 days.

(21) Appl. No.: 11/638,573

(22) Filed: Dec. 14, 2006

(65) Prior Publication Data

US 2007/0090411 A1 Apr. 26, 2007

Related U.S. Application Data

(62) Division of application No. 10/766,018, filed on Jan. 29, 2004, now abandoned.

(30) Foreign Application Priority Data

| Jan. 30, 2003 | (JP) | ............................. 2003-022226 |
| Feb. 12, 2003 | (JP) | ............................. 2003-033761 |
| Mar. 19, 2003 | (JP) | ............................. 2003-074903 |

(51) Int. Cl.
*H01L 29/15* (2006.01)
(52) U.S. Cl. .................... 257/9; 257/E29.076; 356/445
(58) Field of Classification Search .............. 257/9, 257/E29.076; 356/301, 319, 320, 445; 428/117, 428/304.4, 402
See application file for complete search history.

(56) References Cited

U.S. PATENT DOCUMENTS

| 4,014,756 A | 3/1977 | Fromson |
| 5,492,011 A | 2/1996 | Amano et al. |
| 5,499,535 A | 3/1996 | Amano et al. |
| 5,503,034 A | 4/1996 | Amano et al. |
| 5,753,322 A | 5/1998 | Yamaguchi et al. |

(Continued)

FOREIGN PATENT DOCUMENTS

EP 0 822 407 A2 2/1998

(Continued)

OTHER PUBLICATIONS

Goad et al.; Colloidal metal in aluminum-oxide; May 1978; Journal of Applied Physics; vol. 49, Issue No. 5, pp. 2929-2934.*

(Continued)

*Primary Examiner*—Marcos D. Pizarro
(74) *Attorney, Agent, or Firm*—Sughrue Mion, PLLC

(57) ABSTRACT

A sensor chip includes a layer-shaped base body, which has a plurality of fine holes formed in one surface, and fine metal particles, each of which is loaded in one of the fine holes of the base body. At least a part of each of the fine metal particles is exposed to a side of the layer-shaped base body, which side is more outward than the one surface of the layer-shaped base body. The layer-shaped base body may be constituted of anodic oxidation alumina. The sensor chip constitutes a sensor utilizing localized plasmon resonance, with which a state of binding of a sensing medium with a specific substance is capable of being detected quickly and with a high sensitivity.

2 Claims, 13 Drawing Sheets

U.S. PATENT DOCUMENTS

| | | | |
|---|---|---|---|
| 6,034,468 | A | 3/2000 | Wilshaw |
| 6,242,263 | B1 | 6/2001 | Faber et al. |
| 6,350,389 | B1 | 2/2002 | Fujishima et al. |
| 2002/0089617 | A1 | 7/2002 | Fukata et al. |
| 2003/0077839 | A1* | 4/2003 | Takei .......................... 436/177 |

FOREIGN PATENT DOCUMENTS

| | | |
|---|---|---|
| EP | 0 965 835 A2 | 12/1999 |
| JP | 4-173992 A | 6/1992 |
| JP | 6-288843 A | 10/1994 |
| JP | 8-296060 A | 11/1996 |
| JP | 10-332675 A | 12/1998 |
| JP | 11-200090 A | 7/1999 |
| JP | 2000-1393 A | 1/2000 |
| JP | 2000-15098 A | 1/2000 |
| JP | 2000-243247 A | 9/2000 |
| JP | 2000-356587 A | 12/2000 |
| JP | 2002-314245 A | 10/2002 |
| WO | WO 98/37417 A1 | 8/1998 |

OTHER PUBLICATIONS

Andersson et al.; Nickel pigmented anodic aluminum oxide for selective absorption of solar energy; Jan. 1980; Journal of Applied Physics; vol. 51; Issue No. 1; pp. 754-764.*

G.A. Niklasson et al., "Optical Properties of Square Lattices of Gold Nanoparticles", NanoStructured Materials, vol. 12, 1999, pp. 725-730.

El-Kouedi M et al: "Optical properties of gold-silver iodide nanoparticle pair structures", Journal of Physical Chemistry B, May 4, 2000, ACS, USA, vol. 104, No. 17, pp. 4031-4037, XP002289393.

Japanese Abstract No. 03201530, dated Sep. 3, 1991.

Preston C B et al: "Optical characterization of anodic aluminum oxide films containing electrochemically deposited metal particles. 1. Gold in phosphoric acid anodic aluminum oxide films", Journal of Physical Chemistry, Aug. 12, 1993, USA, vol. 97., No. 32, pp. 8495-8503, XP002289394.

Kume T et al: "Interaction between localized and propagating surface plasmons: Ag fine particles on Al surface", Solid State Communications, Jan. 1995, USA, vol. 93, No. 2, pp. 171-175, XP002289395.

Furneaux R C et al: "The formation of controlled-porosity membranes from anodically oxidized aluminum", Nature, Macmillan Journals Ltd. London, GB, vol. 337, No. 6203, Jan. 12, 1989, pp. 147-149, XP002121054.

Hulteen JC et al., "A General Template-Based Method for the Preparation of Nanomaterials", Journal of Materials Chemistry, The Royal Society of Chemistry, Cambridge, GB, vol. 7, No. 7, Jul. 1, 1997, pp. 1075-1087, XP000703793.

David G. W. Goad, et al., "Colloidal Metal in Aluminum-Oxide", J. Appl. Phys. vol. 49, No. 5, pp. 2929-2934, May 1978.

A. Andersson, et al., "Nickel Pigmented Anodic Aluminum Oxide for Selective Absorption of Solar Energy", J. Appl. Phys., vol. 51, No. 1, pp. 754-764, Jan. 1980.

Masashi Nakao, et al., "GaAs and InP Nanohole Arrays Fabricated by Reactive Beam Etching Using Highly Ordered Alumina Membranes", Jpn. J. Appl. Phys., vol. 38, pp. 1052-1055, Part 1, No. 2B, Feb. 1999.

* cited by examiner

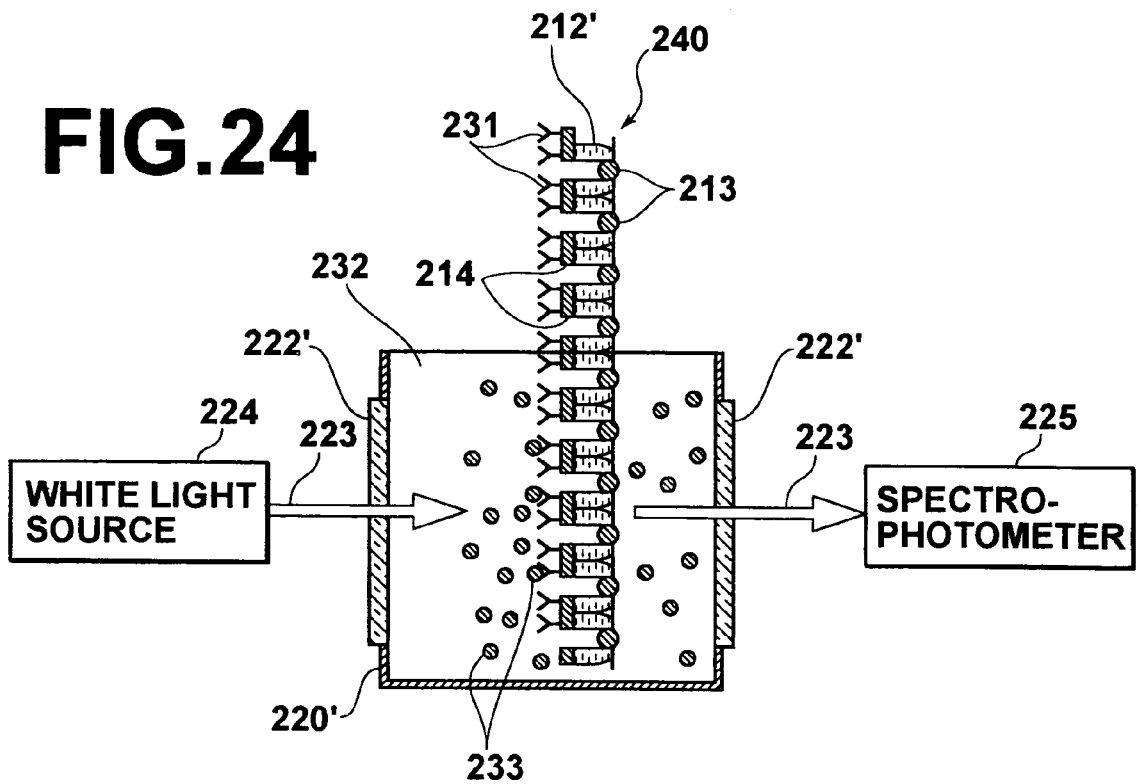
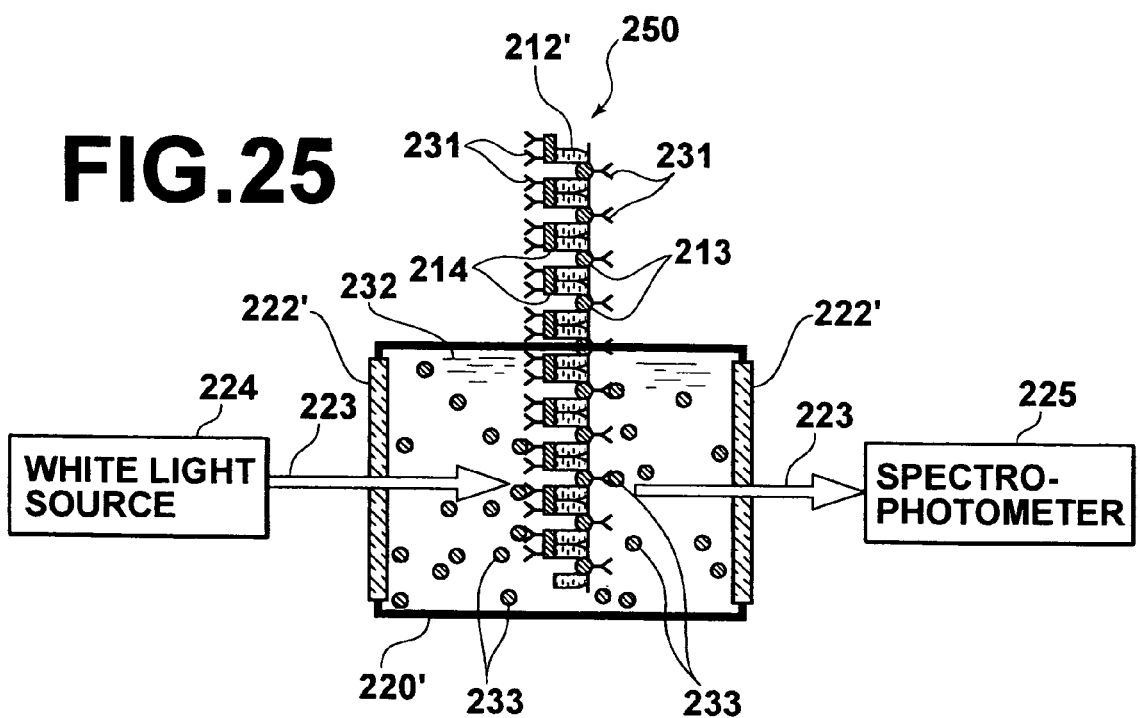

SENSOR INCLUDING POROUS BODY WITH METAL PARTICLES LOADED IN THE PORES OF THE BODY AND MEASURING APPARATUS USING THE SAME

CROSS REFERENCE TO RELATED APPLICATIONS

This is a divisional of application Ser. No. 10/766,018 filed Jan. 29, 2004, now abandoned the disclosure of which is hereby incorporated by reference.

BACKGROUND OF THE INVENTION

1. Field of the Invention

This invention relates to a sensor utilizing localized plasmon resonance. This invention also relates to a sensor chip for use in the sensor, and a process for producing the sensor chip. This invention further relates to a fine structure body for use in the sensor of the type described above, and a process for producing the fine structure body.

2. Description of the Related Art

As disclosed in, for example, Patent Literature 1, there have heretofore been known sensors, in which a fine structure body comprising a dielectric material, a semiconductor, or the like, and fine metal particles secured in a layer-shaped form to a surface of the dielectric material, the semiconductor, or the like, is employed as a sensor chip, and with which a refractive index of a sample, or the like, is measured by the utilization of localized plasmon resonance. Basically, the sensors are provided with means for irradiation measuring light to the area of the fine metal particles of the sensor chip, and photo detecting means for detecting intensity of the measuring light coming from the fine metal particles secured in the layer-shaped form (i.e., the measuring light, which has passed through the fine metal particles, or the measuring light, which has been reflected from the fine metal particles).

With the sensors described above, when the measuring light is irradiated to the area of the fine metal particles secured in the layer-shaped form, the localized plasmon resonance occurs at a certain specific wavelength, and the scattering and the absorption of the measuring light are caused by the localized plasmon resonance to increase markedly. Therefore, in cases where the intensity of the measuring light coming from the fine metal particles secured in the layer-shaped form is detected, the markedly occurring attenuation of the detected intensity of the measuring light is capable of being observed, and the occurrence of the localized plasmon resonance is thereby capable of being confirmed.

In such cases, the light wavelength, at which the localized plasmon resonance occurs, and the extent of the scattering and the absorption of the measuring light depend upon the refractive index of the medium, which is present around the fine metal particles. Specifically, in cases where the refractive index of the medium, which is present around the fine metal particles, is large, a resonance peak wavelength shifts to the long wavelength side, and the scattering and the absorption of the measuring light increase. Therefore, in cases where the measuring light is irradiated to the area of the fine metal particles in a state in which a sample is located around the fine metal particles secured in the layer-shaped form, and the intensity of the measuring light coming from the area of the fine metal particles is detected, the refractive index of the sample, physical properties of the sample corresponding to the refractive index, and the like, are capable of being measured.

In such cases, white light may be employed as the measuring light, the light coming from the area of the fine metal particles may be detected spectrophotometrically, and the shift of the resonance peak wavelength described above may thereby be detected. Alternatively, monochromatic light may be employed as the measuring light, and the shift of the resonance peak wavelength described above, and a change in light intensity accompanying a change in scattering and absorption of the measuring light may thereby be detected.

Also, in order for the measuring light coming from the fine metal particles secured in the layer-shaped form to be detected, a photodetector may be located on the side with respect to the fine metal particles, which side is opposite to the measuring light irradiation side, and the light having passed through the fine metal particles may thereby be detected. Alternatively, the photodetector may be located on the side with respect to the fine metal particles, which side is identical with the measuring light irradiation side, and the light having been reflected from the fine metal particles may thereby be detected. In the latter cases, a base body, to which the fine metal particles are secured in the layer-shaped form, may be made from a material having light reflecting properties. In such cases, the measuring light having passed through the fine metal particles is reflected from the base body. Therefore, the measuring light, which has passed through the fine metal particles and has then been reflected from the base body, is capable of being detected together with the measuring light, which has been reflected from the fine metal particles.

Further, in cases where a sensing medium, which is capable of binding with a specific substance, is fixed to peripheral areas of the fine metal particles of the sensor chip, the refractive index at the peripheral areas of the fine metal particles alters in accordance with the occurrence of the binding of the sensing medium with the specific substance. Therefore, the measuring light may be irradiated to the area of the fine metal particles in the state in which the sensing medium described above has been fixed to the peripheral areas of the fine metal particles, and the intensity of the measuring light coming from the area of the fine metal particles may be detected. In this manner, the occurrence of the binding of the sensing medium with the specific substance is capable of being detected. The combination of the specific substance and the sensing medium may be, for example, the combination of an antigen and an antibody.

As the sensor chip for use in the sensor utilizing the localized plasmon resonance, for example, a sensor chip comprising a base body and a colloidal metal single layer film, which is formed at a surface area of the base body, has heretofore been known. The sensor chip comprising the base body and the colloidal metal single-layer film, which is formed at the surface area of the base body, is described in, for example, Patent Literature 1. Also, a fine structure body comprising layer-shaped anodic oxidation alumina, which has a plurality of fine holes formed in one surface, and fine metal particles, which are loaded in the fine holes of the anodic oxidation alumina, is applicable to the sensor described above. The aforesaid fine structure body is described in, for example, Non-Patent Literatures 1 and 2. Anodic oxidation alumina itself, which has a plurality of fine holes, is also described in, for example, Patent Literature 2 and Non-Patent Literature 3.

As described in, for example, Non-Patent Literature 3, it has also been known that a plurality of fine holes having diameters ranging from approximately several nanometers to approximately 300 nm are formed in a regular pattern in an anodic oxidation alumina film which is obtained from anodic oxidation processing performed with Al in a solution.

A marked feature of the anodic oxidation alumina acting as a porous material is that the anodic oxidation alumina has a honeycomb structure, in which the fine holes are formed in parallel at approximately equal intervals and extend in a direction approximately normal to the surface of the base plate. The anodic oxidation alumina also has the unique features in that the diameters of the fine holes, the intervals of the fine holes, and the depths of the fine holes are capable of being adjusted comparatively freely.

As described in, for example, Non-Patent Literature 4, it has also been known that an anodic oxidation alumina film may be formed on a base plate constituted of GaAs or InP, and fine holes may be formed in the GaAs base plate or the InP base plate with the anodic oxidation alumina film acting as a mask.

[Patent Literature 1]
U.S. Patent Laid-Open No. 20020089617

[Patent Literature 2]
Japanese Unexamined Patent Publication No. 11(1999)-200090

[Non-Patent Literature 1]
Journal of Applied Physics, Vol. 49, No. 5, p. 2929, 1978

[Non-Patent Literature 2]
Journal of Applied Physics, Vol. 51, No. 1, p. 754, 1980

[Non-Patent Literature 3]
"High-Regularity Metal Nano-Hole Array Based on Anodized Alumina" by Hideki Masuda, Solid Physics, Vol. 31, No. 5, p. 493, 1996

[Non-Patent Literature 4]
Masashi Nakano, et al., Jpn. J. Appl. Phys., Vol. 38, pp. 1052-1055, 1999

A sensor chip comprising the layer-shaped base body, such as the anodic oxidation alumina, which has the plurality of the fine holes formed in one surface as described above, and the fine metal particles, which are loaded in the fine holes of the base body, is also capable of being used for the operation, in which the sensing medium, which is capable of binding with the specific substance, is fixed to peripheral areas of the fine metal particles, and the occurrence of the binding of the sensing medium with the specific substance is thereby detected.

However, in cases where the state of the binding of the sensing medium with the specific substance is to be detected by use of the conventional sensor chip constituted in the manner described above, the problems are encountered in that the change in sensor output signal arising due to the occurrence of the binding of the sensing medium with the specific substance (i.e., the shift of the resonance peak wavelength described above, or the change in light intensity accompanying a change in scattering and absorption of the measuring light) is weak, and a long period of time is required before the change in sensor output signal arising due to the occurrence of the binding of the sensing medium with the specific substance is found.

SUMMARY OF THE INVENTION

In view of the above circumstances, the first object of the present invention is to provide a sensor utilizing localized plasmon resonance, with which a state of binding of a sensing medium with a specific substance is capable of being detected quickly and with a high sensitivity, and a sensor chip for use in the sensor.

In the cases of the anodic oxidation alumina film described above, due to features of crystal growth, a region in which the composition is nonuniform occurs between the holes. Therefore, the problems occur in that, in cases where the anodic oxidation alumina film is used in a sensor, or the like, the nonuniformity of the composition causes optical noise to occur and obstructs enhancement of a signal-to-noise ratio.

In view of the above circumstances, the second object of the present invention is to provide a sensor chip for use in a sensor wherein a state of localized plasmon resonance at a surface of each of fine metal particles is detected by the utilization of light and wherein characteristics of a sample in the vicinity of each of the fine metal particles are thereby analyzed, which sensor chip allows measurement with little noise and with a high sensitivity, a process for producing the sensor chip, and a sensor using the sensor chip.

In the cases of the sensor using the conventional fine structure body described above, the attenuation of the measuring light due to the localized plasmon resonance occurs over a comparatively wide wavelength range around the resonance peak wavelength. Specifically, with the sensor using the conventional fine structure body, the measuring light absorption and scattering spectral characteristics do not alter sufficiently sharply. Therefore, with the conventional sensor, the problems occur in that a slight change in refractive index of a sample or physical properties of the sample and slight binding of a specific substance with a fixed substance cannot always be detected.

In view of the above circumstances, the third object of the present invention is to provide a sensor utilizing localized plasmon resonance, with which a slight change in refractive index of a sample or a slight change in physical properties of the sample is capable of being detected, a fine structure body for use in the sensor, and a process for producing the fine structure body.

A first sensor chip in accordance with the present invention aims at accomplishing the aforesaid first object of the present invention. Specifically, the present invention provides a first sensor chip, comprising:

i) a layer-shaped base body, which has a plurality of fine holes formed in one surface, and ii) fine metal particles, each of which is loaded in one of the fine holes of the base body, wherein at least a part of each of the fine metal particles is exposed to a side of the layer-shaped base body, which side is more outward than the one surface of the layer-shaped base body.

The first sensor chip in accordance with the present invention should preferably be modified such that the layer-shaped base body is constituted of anodic oxidation alumina. Alternatively, the first sensor chip in accordance with the present invention may be modified such that the fine holes of the layer-shaped base body are formed with etching processing, in which anodic oxidation alumina having a plurality of fine holes is utilized as a mask.

Also, the first sensor chip in accordance with the present invention should preferably be modified such that at least a one-half part of each of the fine metal particles is exposed to the side of the layer-shaped base body, which side is more outward than the one surface of the layer-shaped base body. Further, the first sensor chip in accordance with the present invention should preferably be modified such that a diameter of each of the fine metal particles is at most 200 nm.

The present invention also provides a first sensor using the aforesaid first sensor chip in accordance with the present invention, the sensor comprising:

i) means for irradiating measuring light to an area of the fine metal particles of the sensor chip, and ii) photo detecting means for detecting intensity of the measuring light, which has passed through the area of the fine metal particles, or has been reflected from the area of the fine metal particles.

The first sensor in accordance with the present invention should preferably be modified such that the means for irradiating the measuring light is means for producing white light as the measuring light, and the photo detecting means spectrophotometrically detects the intensity of the measuring light, which has passed through the area of the fine metal particles, or has been reflected from the area of the fine metal particles.

A second sensor chip in accordance with the present invention aims at accomplishing the aforesaid second object of the present invention. Specifically, the present invention further provides a second sensor chip for use in a sensor wherein a state of localized plasmon resonance at a surface of each of fine metal particles is detected by the utilization of light and wherein characteristics of a sample in the vicinity of each of the fine metal particles are thereby analyzed, the sensor chip comprising:

i) a support member having a plurality of independent fine holes, which extend in a direction approximately normal to a surface of the support member, and ii) independent fine metal particles, each of which is supported within one of the fine holes of the support member, wherein the support member is constituted of a transparent dielectric material having uniform density.

The second sensor chip in accordance with the present invention should preferably be modified such that the support member is constituted of a polystyrene.

The present invention still further provides a process for producing the aforesaid second sensor chip in accordance with the present invention. Specifically, the present invention still further provides a process for producing a sensor chip, comprising the steps of:

i) forming an anodic oxidation alumina film on a surface of a base plate, which is constituted of a transparent dielectric material, the anodic oxidation alumina film having a plurality of first fine holes, which extend in a direction approximately normal to the surface of the base plate, ii) subjecting the base plate to etching processing, in which the anodic oxidation alumina film having been formed on the surface of the base plate is utilized as a mask, a plurality of second fine holes, each of which corresponds to one of the first fine holes, being thereby formed in the surface of the base plate, and iii) performing processing wherein, after the anodic oxidation alumina film has been removed from the surface of the base plate, a metal depositing operation is performed on the base plate having the surface, in which the second fine holes have been formed, the metal depositing operation being performed from the side of the surface of the base plate, and a metal deposit layer having been formed on the surface of the base plate is then removed, whereby each of independent fine metal particles is supported within one of the second fine holes of the base plate.

The present invention also provides a second sensor, comprising:

i) the aforesaid second sensor chip in accordance with the present invention, ii) a light source for producing light, such that the light impinges upon an area of the fine metal particles of the sensor chip, and iii) photo detecting means for detecting intensity of the light, which has passed through the area of the fine metal particles of the sensor chip, or has been reflected from the area of the fine metal particles of the sensor chip, wherein characteristics of a sample in the vicinity of each of the fine metal particles, each of which is supported within one of the fine holes of the support member, are analyzed in accordance with results of measurement obtained from the photo detecting means.

The second sensor in accordance with the present invention should preferably be modified such that the photo detecting means is a spectrophotometer.

The term "uniform density" as used herein means the density such that optical noise does not occur when the sensor chip is used in the sensor, and such that little nonuniform composition region, little defect due to nonuniform composition, or the like, is present.

The term "transparent dielectric material" as used herein means the dielectric material, which substantially transmits the measuring light for the detection of the localized plasmon resonance, i.e. the light produced by the light source.

The term "vicinity of each of fine metal particles" as used herein means the range from the surface of each of the fine metal particles to a region located at a distance approximately equal to the diameter of each of the fine metal particles, i.e. the range in which the localized plasmon resonance occurs.

A fine structure body in accordance with the present invention aims at accomplishing the aforesaid third object of the present invention. Specifically, the present invention further provides a fine structure body, comprising:

i) a layer-shaped base body, which has a plurality of fine holes formed in one surface, ii) fine metal particles, each of which is loaded in one of the fine holes of the base body, and iii) a thin metal film formed on areas of the one surface of the layer-shaped base body, which areas are located around each of the fine holes of the layer-shaped base body, such that the thin metal film is located at a spacing, which is approximately equal to at most a diameter of each of the fine metal particles, from each of the fine metal particles.

The fine structure body in accordance with the present invention should preferably be modified such that the layer-shaped base body is constituted of anodic oxidation alumina. Alternatively, the fine structure body in accordance with the present invention may be modified such that the fine holes of the layer-shaped base body are formed with etching processing, in which anodic oxidation alumina having a plurality of fine holes is utilized as a mask.

Also, the fine structure body in accordance with the present invention should preferably be modified such that the layer-shaped base body is transparent with respect to light irradiated to the layer-shaped base body.

Further, the fine structure body in accordance with the present invention should preferably be modified such that the layer-shaped base body is divided into a plurality of layer-shaped base sub-bodies, which are located at a spacing from one another and are supported together with one another.

The present invention still further provides a process for producing the aforesaid fine structure body in accordance with the present invention, comprising the steps of:

i) obtaining the layer-shaped base body, which has the plurality of the fine holes formed in the one surface, and ii) performing vacuum evaporation processing from the side of the one surface of the layer-shaped base body, whereby each of the fine metal particles is loaded in one of the fine holes of the base body, and the thin metal film is formed on the areas of the one surface of the layer-shaped base body, which areas are located around each of the fine holes of the layer-shaped base body.

The present invention also provides a process for producing the aforesaid fine structure body in accordance with the present invention, comprising the steps of:

i) obtaining the layer-shaped base body, which has the plurality of the fine holes formed in the one surface, ii) performing plating processing on the layer-shaped base body, each of the fine metal particles being thereby loaded in one of the fine holes of the base body, and iii) performing vacuum evaporation processing from the side of the one surface of the layer-shaped base body, whereby the thin metal film is formed on the areas of the one surface of the layer-shaped base body, which areas are located around each of the fine holes of the layer-shaped base body.

The present invention further provides a third sensor using the aforesaid fine structure body in accordance with the present invention, the sensor comprising:

i) means for irradiating measuring light to an area of the fine metal particles and the thin metal film of the fine structure body, and ii) photo detecting means for detecting intensity of the measuring light, which has passed through the area of the fine metal particles and the thin metal film, or has been reflected from the area of the fine metal particles and the thin metal film.

The third sensor in accordance with the present invention should preferably be modified such that the photo detecting means spectrophotometrically detects the intensity of the measuring light, which has passed through the area of the fine metal particles and the thin metal film, or has been reflected from the area of the fine metal particles and the thin metal film.

Effects of the present invention will be described hereinbelow.

The inventors conducted extensive research and found that the problems, which are encountered with the conventional technique and which the present invention aims at solving as the first object described above, occur for the reasons described below.

Specifically, with the conventional sensor chip, each of the fine metal particles, which is loaded within one of the fine holes of the base body, such as the anodic oxidation alumina, is formed in a tightly loaded state (i.e., such that no space is present between the fine metal particle and the peripheral wall of the fine hole. Therefore, the sensing medium is fixed to only the surface area of the fine metal particle, which surface area stands facing the inlet side of the fine hole, and the amount of the sensing medium fixed to the fine metal particle is markedly small. Accordingly, the change in refractive index at the peripheral area of the fine metal particle, which change occurs due to the binding of the sensing medium with the specific substance, is small, and a large change in sensor output signal cannot be obtained.

Also, with the conventional sensor chip, each of the fine metal particles is fixed to the bottom of one of the deep fine holes of the base body, and therefore the sensing medium fixed to the fine metal particle is present at the deep position in the fine hole. Therefore, the specific substance is capable of binding with the sensing medium only after the specific substance has diffused within the fine hole to the position in the vicinity of the bottom of the fine hole. However, a long period of time is required for the specific substance to diffuse within the fine hole to the position in the vicinity of the bottom of the fine hole. Accordingly, a long period of time is required before the change in sensor output signal is found.

With the first sensor chip in accordance with the present invention, in accordance with the newly obtained findings described above, at least a part of each of the fine metal particles is exposed to the side of the layer-shaped base body, which side is more outward than the one surface of the layer-shaped base body. Therefore, the sensing medium is capable of being fixed to side surface areas, and the like, of each of the fine metal particles. Accordingly, the amount of the sensing medium fixed to each of the fine metal particles becomes large, and the change in refractive index at the peripheral area of each of the fine metal particles, which change occurs due to the binding of the sensing medium with the specific substance, becomes large. As a result, a large change in sensor output signal is capable of being obtained. Therefore, with the first sensor chip in accordance with the present invention, an accurate analysis is capable of being performed.

Also, with the first sensor chip in accordance with the present invention, wherein each of the fine metal particles, to which the sensing medium is fixed, is located in the state described above, the specific substance need not diffuse within the fine hole to the position in the vicinity of the bottom of the fine hole and is capable of binding with the sensing medium. Therefore, the change in sensor output signal due to the binding of the specific substance with the sensing medium is capable of being found quickly, and the efficiency with which the sample analysis is made is capable of being enhanced.

The anodic oxidation alumina described above is formed as a porous oxide film on the surface of aluminum with processing, wherein aluminum is subjected to anodic oxidation in an acidic electrolyte. The anodic oxidation alumina has the features such that a plurality of markedly fine holes having diameters ranging from approximately several nanometers to approximately several hundreds of nanometers are formed as independent fine holes extending in the direction approximately normal to the surface of the anodic oxidation alumina, and such that the fine holes are formed at approximately equal intervals. Also, the anodic oxidation alumina has the features such that the diameters of the fine holes, the intervals of the fine holes, and the depths of the fine holes are capable of being adjusted comparatively freely by adjustment of conditions for the anodic oxidation. (The features of the anodic oxidation alumina are described in, for example, Non-Patent Literature 3 described above.) During a process for producing the first sensor chip in accordance with the present invention, in order for at least a part of each of the fine metal particles to be exposed to the side of the layer-shaped base body, which side is more outward than the one surface of the layer-shaped base body, the depths of the fine holes of the base body may be adjusted accurately. Therefore, the anodic oxidation alumina having the features described above is markedly appropriate as the material for constituting the layer-shaped base body.

The anodic oxidation alumina described above may be used directly in the state in which the anodic oxidation alumina has been formed as a film on the surface of aluminum. Alternatively, the anodic oxidation alumina having been formed on the surface of aluminum may be separated from the surface of aluminum and may then be used in the state in which the anodic oxidation alumina has been separated from the surface of aluminum. As another alternative, the anodic oxidation alumina having been formed on the surface of aluminum may be separated from the surface of aluminum and may then be used in a state in which the anodic oxidation alumina has been secured onto a different base plate.

With the second sensor chip in accordance with the present invention, wherein the support member is constituted of the transparent dielectric material having uniform density, optical noise is capable of being prevented from occurring, and measurement with a high sensitivity is capable of being performed.

With the second sensor chip in accordance with the present invention, wherein the transparent dielectric material is constituted of a polystyrene, in cases where the second sensor chip in accordance with the present invention is utilized for enzyme immunoassay techniques, such as enzyme-linked immunosorbent assay techniques (ELISA techniques), noise due to non-specific adsorption is capable of being suppressed by virtue of the characteristics of the polystyrene undergoing little non-specific adsorption of proteins. Therefore, measurement with a high sensitivity is capable of being performed.

With the process for producing a sensor chip in accordance with the present invention, the fine holes are capable of being located at a high density in the support member, which is constituted of the transparent dielectric material capable of substantially transmitting the measuring light, and a sensor chip having a high sensitivity is capable of being obtained. Also, the sizes of the fine metal particles are capable of being set at arbitrary sizes, and various sensor chips appropriate for the purposes of use of the sensor chips are capable of being obtained.

With the second sensor in accordance with the present invention, wherein the second sensor chip in accordance with the present invention having the effects of suppressing optical noise and enabling measurement with a high sensitivity is used, analysis of a sample is capable of being performed with a high sensitivity.

The fine structure body in accordance with the present invention comprises the layer-shaped base body, which has the plurality of the fine holes formed in one surface, and the fine metal particles, each of which is loaded in one of the fine holes of the base body. Therefore, in cases where the fine structure body in accordance with the present invention is used as a sensor unit as in the cases of the conventional sensor described above, in which the localized plasmon resonance is utilized, the refractive index of a sample located at the peripheral areas of the fine metal particles, physical properties of the sample corresponding to the refractive index, the occurrence of the binding of a sensing medium, which is located at the peripheral areas of the fine metal particles, with a specific substance, and the like, are capable of being detected.

Also, the fine structure body in accordance with the present invention comprises the thin metal film formed on the areas of the one surface of the layer-shaped base body, which areas are located around each of the fine holes of the layer-shaped base body, such that the thin metal film is located at the spacing, which is approximately equal to at most the diameter of each of the fine metal particles, from each of the fine metal particles. Therefore, near field light, which occurs when the measuring light is irradiated to an area of the fine metal particles, interacts with the thin metal film, and an absorption spectrum due to electric multipoles occurs with the measuring light.

Also, with the fine structure body in accordance with the present invention, wherein the layer-shaped base body is transparent with respect to the light irradiated to the layer-shaped base body, surface plasmon resonance is excited by the interaction between the light totally reflected within the layer-shaped base body and the thin metal film.

Therefore, in cases where the fine structure body in accordance with the present invention is used in a sensor utilizing the localized plasmon resonance, the measuring light absorption and scattering spectral characteristics alter sufficiently sharply due to the synergistic effects of the localized plasmon resonance and the electric multipoles, or the synergistic effects of the localized plasmon resonance, the electric multipoles, and the surface plasmon resonance. The third sensor using the fine structure body in accordance with the present invention comprises: (i) the means for irradiating the measuring light to the area of the fine metal particles and the thin metal film of the fine structure body, and (ii) the photo detecting means for detecting the intensity of the measuring light, which has passed through the area of the fine metal particles and the thin metal film, or has been reflected from the area of the fine metal particles and the thin metal film. Accordingly, with the third sensor using the fine structure body in accordance with the present invention, a slight change in refractive index of a sample or physical properties of the sample and slight binding of a specific substance with a sensing medium are capable of being detected.

As described above, the fine structure body in accordance with the present invention is capable of being use appropriately in a sensor utilizing the localized plasmon resonance. The fine structure body in accordance with the present invention is also applicable to a light modulating device, wherein light to be modulated is irradiated to the area of the fine metal particles and the thin metal film, the refractive index of a medium located around the area of the fine metal particles and the thin metal film is caused to alter, and the light to be modulated is thereby modulated. In cases where the fine structure body in accordance with the present invention is applied to the light modulating device described above, a large extinction ratio is capable of being obtained in accordance with the slight change in refractive index of the medium described above.

As described above, the anodic oxidation alumina described above is formed as a porous oxide film on the surface of aluminum with processing, wherein aluminum is subjected to anodic oxidation in an acidic electrolyte. The anodic oxidation alumina has the features such that a plurality of markedly fine holes having diameters ranging from approximately several nanometers to approximately several hundreds of nanometers are formed as independent fine holes extending in the direction approximately normal to the surface of the anodic oxidation alumina, and such that the fine holes are formed at approximately equal intervals. Also, the anodic oxidation alumina has the features such that the diameters of the fine holes, the intervals of the fine holes, and the depths of the fine holes are capable of being adjusted comparatively freely by adjustment of conditions for the anodic oxidation. (The features of the anodic oxidation alumina are described in, for example, Non-Patent Literature 3 described above.) During the process for producing the fine structure body in accordance with the present invention, in order for each of the fine metal particles and and the thin metal film to be located such that the thin metal film is located at the spacing, which is approximately equal to at most the diameter of each of the fine metal particles, from each of the fine metal particles, the depths of the fine holes of the base body may be adjusted accurately. Therefore, the anodic oxidation alumina having the features described above is markedly appropriate as the material for constituting the layer-shaped base body of the fine structure body in accordance with the present invention.

The aforesaid anodic oxidation alumina for constituting the layer-shaped base body of the fine structure body in accordance with the present invention may be used directly in the state in which the anodic oxidation alumina has been formed as a film on the surface of aluminum. Alternatively, the anodic oxidation alumina having been formed on the surface of aluminum may be separated from the surface of aluminum and may then be used in the state in which the anodic oxidation alumina has been separated from the surface of aluminum. As another alternative, the anodic oxidation alumina having been formed on the surface of aluminum may be separated from the surface of aluminum and may then be used in a state in which the anodic oxidation alumina has been secured onto a different base plate.

With the fine structure body in accordance with the present invention, wherein the layer-shaped base body is divided into the plurality of the layer-shaped base sub-bodies, which are located at a spacing from one another and are supported together with one another, each of the layer-shaped base sub-bodies is capable of being dipped in to one of wells of a micro-titer plate, which wells have been filled with different samples. Therefore, the different samples having been filled in the wells of the micro-titer plate are capable of being supplied simultaneously to the respective layer-shaped base sub-bodies (i.e., the fine metal particles and the thin metal films, which are supported by the layer-shaped base sub-bodies). In such cases, the efficiency of the sample supplying operation is capable of being enhanced. Also, the measuring light is capable of being irradiated simultaneously to the layer-shaped base sub-bodies. Alternatively, the measuring light is capable of being irradiated successively at short time intervals to the layer-shaped base sub-bodies. As a result, the efficiency with which the detection of the measuring light is performed is capable of being enhanced. Accordingly, analyses and measurements of a large number of samples are capable of being performed quickly.

BRIEF DESCRIPTION OF THE DRAWINGS

FIG. 24 is a schematic side view showing a further different embodiment of the fine structure body in accordance with the present invention and a further different embodiment of the third sensor in accordance with the present invention, FIG. 25 is a schematic side view showing a still further different embodiment of the fine structure body in accordance with the present invention and a still further different embodiment of the third sensor in accordance with the present invention.

DESCRIPTION OF THE PREFERRED EMBODIMENTS

The present invention will hereinbelow be described in further detail with reference to the accompanying drawings.

Figure 1:
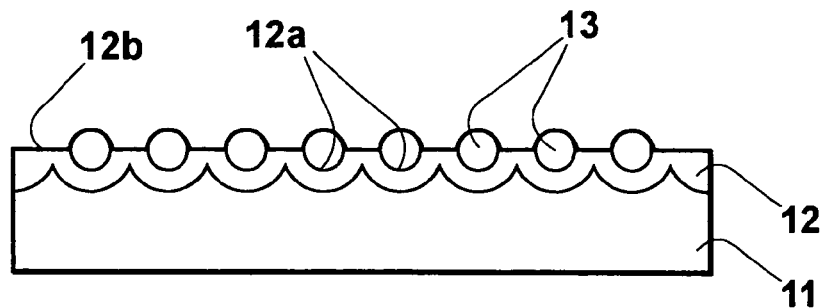
FIG. 1 is a schematic side view showing an embodiment of the first sensor chip in accordance with the present invention.

FIG. 1 is a schematic side view showing a sensor chip 10, which is an embodiment of the first sensor chip in accordance with the present invention. As illustrated in FIG. 1, the sensor chip 10 comprises an aluminum base plate 11. The sensor chip 10 also comprises anodic oxidation alumina 12, which is formed on the aluminum base plate 11 and acts as the layer-shaped base body. The anodic oxidation alumina 12 has a plurality of fine holes 12a, 12a, . . . , which are formed in one surface (the upper surface in FIG. 1) 12b. The sensor chip 10 further comprises fine gold (Au) particles 13, 13, . . . , each of which is loaded in one of the fine holes 12a, 12a, . . . In this embodiment of the sensor chip 10, each of the fine gold particles 13, 13, . . . loaded on the bottoms of the fine holes 12a, 12a, . . . has a diameter of approximately 200 nm. Each of the fine gold particles 13, 13, . . . should preferably have a diameter falling within the range of, for example, approximately several nanometers to approximately 100 nm. Also, the depth of each of the fine holes 12a, 12a, . . . is smaller than the radius of each of the fine gold particles 13, 13, . . . Therefore, at least a one-half part of each of the fine gold particles 13, 13, . . . is exposed to the side of the anodic oxidation alumina 12, which side is more outward than the one surface 12b of the anodic oxidation alumina 12.

By way of example, the sensor chip 10 having the constitution described above may be produced in the manner described below. Specifically, firstly, the aluminum base plate 11 having the surface, on which the film of the anodic oxidation alumina 12 has been formed, is prepared. Thereafter, vacuum evaporation processing with gold is performed on the anodic oxidation alumina 12. The vacuum evaporation processing with gold is performed from the side of the one surface 12b of the anodic oxidation alumina 12, in which surface the fine holes 12a, 12a, ... have been formed. With the vacuum evaporation processing, each of the fine gold particles 13, 13, ... is loaded in one of the fine holes 12a, 12a, ... of the anodic oxidation alumina 12. This embodiment of the sensor chip 10 is thus obtained.

In lieu of the fine gold particles 13, 13, ..., fine metal particles of a different metal, e.g. silver, maybe formed. However, from the view point described below, gold is particularly preferable as the material for the formation of the sensor chip in accordance with the present invention. Specifically, gold has good malleability and good ductility, and therefore the vacuum evaporation processing with gold is capable of being performed appropriately at comparatively low temperatures. Also, since gold has a high corrosion resistance, in cases where the sensor chip 10 provided with the fine gold particles 13, 13, ... is utilized in a sensor, which will be described later, a sensor having stable characteristics is capable of being obtained. Further, the sensor chip 10 provided with the fine gold particles 13, 13, ... is easy to process during the production and the use of the sensor.

Alternatively, the first sensor chip in accordance with the present invention, in which the part of each of the fine metal particles is exposed to the side of the layer-shaped base body, which side is more outward than the one surface of the layer-shaped base body, may be produced in the manner described below. Specifically, firstly, a metal, such as gold or silver, may be loaded in each of the fine holes of the anodic oxidation alumina with vacuum evaporation processing, sputtering processing, plating processing, or the like. Thereafter, the metal clinging to the surface of the anodic oxidation alumina may be wiped off and removed by use of an applicator, or the like. In this manner, each of isolated metal particles is formed in one of the fine holes of the anodic oxidation alumina. Further, the alumina layer may be subjected to etching with a mixed liquid of phosphoric acid (e.g., 6 wt %) and chromic acid (e.g., 1.8 wt %).

The layer-shaped anodic oxidation alumina 12 may be formed on the aluminum base plate 11 in the manner described below. The layer-shaped anodic oxidation alumina 12 may be formed with one of various techniques. Basically, a technique is employed wherein, when the aluminum base plate 11 is subjected to anodic oxidation in an acidic electrolyte, the formation of an oxide film and the dissolution of the oxide film having been formed are allowed to progress simultaneously. With the technique described above, with the dissolving effect of the acid, fine pits (fine holes) occur at random in the surface of the oxide film, which has been formed on the aluminum base plate 11 at the initial stage of the anodic oxidation. Also, as the anodic oxidation progresses, certain pits among the pits described above grow preferentially, and a plurality of pits are thus arrayed at approximately equal intervals in the surface of the oxide film. An area of the oxide film, at which a pit has been formed, is exerted to an electric field, which is stronger than the electric field applied to the other areas of the oxide film. Therefore, the dissolution of the area of the oxide film, at which the pit has been formed, is promoted. As a result, in the layer-shaped anodic oxidation alumina 12, as the layer-shaped anodic oxidation alumina 12 grows, the fine holes 12a, 12a, ... are formed by selective dissolution, and an area, which is not dissolved and remains in the pattern surrounding each of the fine holes 12a, 12a, ..., is formed.

In the anodic oxidation alumina 12 obtained in the manner described above, the plurality of the fine holes 12a, 12a, ... are formed in the regularly arrayed pattern. Each of the fine holes 12a, 12a, ... constitutes a space, which extends in the direction approximately normal to the surface of the anodic oxidation alumina 12. Also, the space constituted by each of the fine holes 12a, 12a, ... has an approximately identical cross-sectional shape and a closed bottom.

Techniques for regulating the positions, at which the fine holes are formed, are disclosed in, for example, Japanese Unexamined Patent Publication Nos. 2001-9800 and 2001-138300. With the disclosed techniques for regulating the positions, at which the fine holes are formed, for example, a converged ion beam is irradiated to aluminum, and dissolution start points are thereby formed at desired positions on the aluminum. Thereafter, the anodic oxidation processing is performed in the manner described above. In this manner, the fine holes 12a, 12a, ... are capable of being formed at the desired positions. Also, by the adjustment of the conditions at the time of the irradiation of the converged ion beam, such as the quantity of irradiation of the converged ion beam, the diameter of the converged ion beam, and the irradiation energy, the recess shapes and compositions of the dissolution start points are capable of being altered. Therefore, the diameters of the finally formed fine holes 12a, 12a, ... are capable of being regulated freely.

Further, as a technique for forming the array of the fine holes 12a, 12a, ... at a particularly high density, for example, a technique wherein oxalic acid is used may be employed. Specifically, oxalic acid may be utilized as the electrolyte for the anodic oxidation, and the anodic oxidation processing may be performed at a predetermined voltage of approximately 40V. In such cases, the fine holes 12a, 12a, ... are capable of being formed in a regularly arrayed pattern and at a high density. The regularity of the array of the fine holes 12a, 12a, ... progresses with the passage of time of anodic oxidation. Therefore, in cases where the anodic oxidation processing is performed for a long period of time, the fine holes 12a, 12a, ..., which are located at a high regularity and at a high density, are capable of being formed.

In the manner described above, the diameters, the intervals, and the depths of the fine holes 12a, 12a, ... are capable of being regulated comparatively freely. Therefore, the fine gold particles 13, 13, ... are capable of being formed with arbitrary uniform size and are capable of being located regularly. As a result, in cases where the sensor chip 10 is used in the sensor, which will be described later, the sensitivity of the sensor is capable of being enhanced and kept stable.

Figure 2:
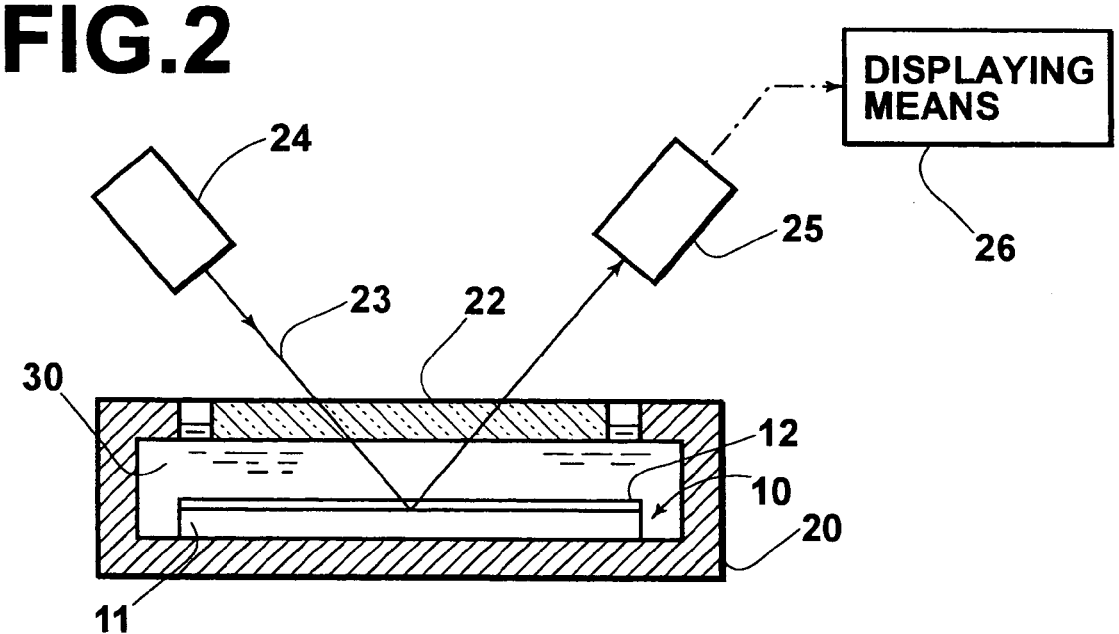
FIG. 2 is a side view showing an embodiment of the first sensor in accordance with the present invention.
Figure 3:
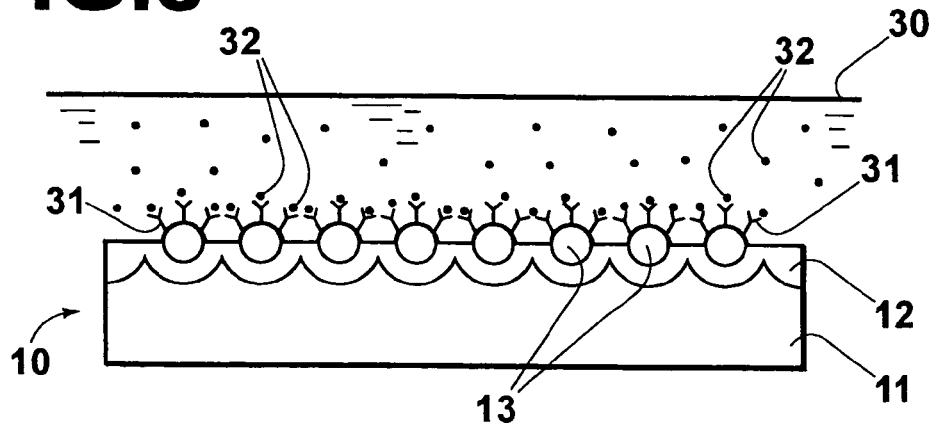
FIG. 3 is a schematic side view showing how the sensor chip of FIG. 1 is used for sample analysis.

An embodiment of the first sensor in accordance with the present invention will be described hereinbelow. FIG. 2 is a side view showing an embodiment of the first sensor in accordance with the present invention, which is constituted as a biosensor using the sensor chip 10 described above. FIG. 3 is an enlarged view showing the part of the sensor chip 10 in the sensor of FIG. 2. As illustrated in FIG. 2, the sensor comprises a vessel 20 having a transparent window 22, which is formed at the top surface of the vessel 20. The sensor chip 10 is secured to the inside bottom surface of the vessel 20. The sensor also comprises a white light source 24 for irradiating measuring light 23 obliquely toward the sensor chip 10 secured to the inside bottom surface of the vessel 20. The sensor further comprises a spectrophotometer 25 for spectrophotometrically detecting the measuring light 23, which has been reflected from the sensor chip 10. The sensor still further comprises displaying means 26 for displaying the results of the spectrophotometric detection.

Before the sensor chip 10 is used in the sensor, an antibody 31 (indicated by the Y-shaped mark in FIG. 3) acting as a sensing medium is fixed to the part of each of the fine gold particles 13, 13, . . . of the sensor chip 10, which part is exposed to the side of the anodic oxidation alumina 12 more outward than the one surface of the anodic oxidation alumina 12. The sensor chip 10 is located within the vessel 20 such that the one surface of the anodic oxidation alumina 12, in which surface the fine gold particles 13, 13, . . . have been loaded, stands facing up. Also, a sample liquid 30 to be analyzed is introduced into the vessel 20 such that the sample liquid 30 comes into contact with the anodic oxidation alumina 12.

The measuring light 23, which is white light, is irradiated through the transparent window 22 of the vessel 20 to the sensor chip 10, which has been located within the vessel 20 in the manner described above. In such cases, the measuring light 23 is reflected from the irradiated area of the fine gold particles 13, 13, . . . (illustrated in FIGS. 1 and 3). The measuring light 23 having thus been reflected from the irradiated area of the fine gold particles 13, 13, . . . is spectrophotometrically detected by the spectrophotometer 25. Also, in such cases, the measuring light 23 passes through the area of the anodic oxidation alumina 12, at which area the fine gold particles 13, 13, . . . are present. The measuring light 23 having passed through the aforesaid area of the anodic oxidation alumina 12 is reflected upwardly from the aluminum base plate 11. The measuring light 23 having thus been reflected upwardly from the aluminum base plate 11 is also spectrophotometrically detected by the spectrophotometer 25.

Figure 4:
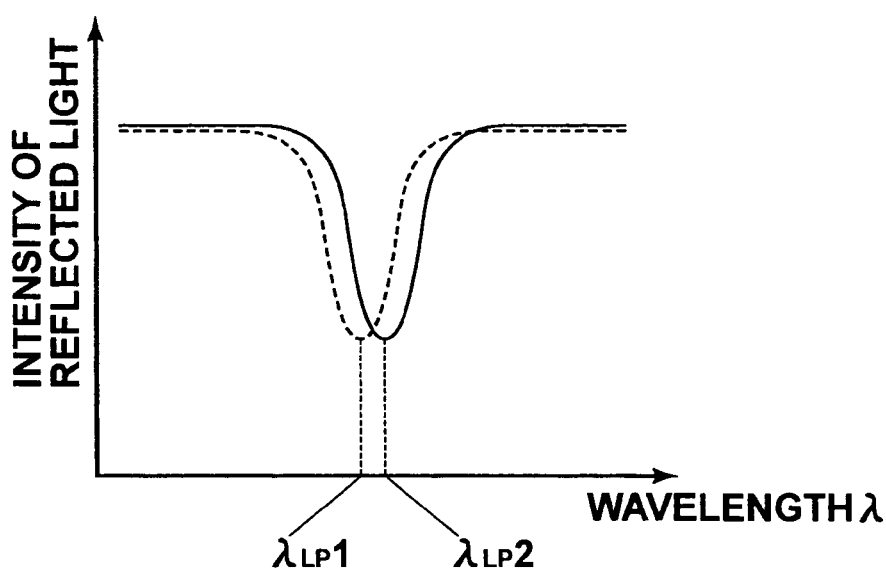
FIG. 4 is a graph showing spectral intensity characteristics of measuring light detected with the sensor shown in FIG. 3.

The reflected light, which is thus detected, has the spectral intensity characteristics basically identical with the spectral intensity characteristics illustrated in FIG. 4. Specifically, in cases where the measuring light 23 is irradiated to the area of the fine gold particles 13, 13, . . . of the anodic oxidation alumina 12, as for a light component having a specific wavelength $\lambda_{LP}$, the scattering and the absorption of the measuring light increase specifically due to the localized plasmon resonance. Therefore, as for the light component having the specific wavelength $\lambda_{LP}$, the intensity of the reflected light becomes markedly low.

At this time, as illustrated in FIG. 3, in cases where a specific antigen 32, which is capable of undergoing specific binding with the antibody 31 described above, is contained in the sample liquid 30, the antigen 32 is bound to the antibody 31 of the sensor chip 10. In cases where the antigen 32 is thus bound to the antibody 31, the refractive index at the peripheral areas of the fine gold particles 13, 13, . . . of the sensor chip 10 changes. As a result, the absorption and scattering spectral characteristics of the measuring light 23 detected by the spectrophotometer 25 change. By way of example, in cases where a resonance peak wavelength is $\lambda_{LP}1$ as indicated by the broken line in FIG. 4 before the binding of the antibody 31 with the antigen 32 arises, the resonance peak wavelength changes to $\lambda_{LP}2$ as indicated by the solid line in FIG. 4 after the binding of the antibody 31 with the antigen 32 arises. As described above, the change in absorption and scattering spectral characteristics of the measuring light 23 detected by the spectrophotometer 25 appears as a shift of the resonance peak wavelength. Therefore, the absorption and scattering spectral characteristics of the measuring light 23 may be detected by the spectrophotometer 25 before the sample liquid 30 is introduced into the vessel 20 and after the sample liquid 30 is introduced into the vessel 20. Also, the results of the detection may be displayed on the displaying means 26. In this manner, from the change in displayed resonance peak wavelength, it is possible to find whether the binding of the antibody 31 with the antigen 32 has or has not occurred, i.e. whether the antigen 32 is or is not present in the sample liquid 30.

The sensor chip 10 used in the sensor is constituted such that the part of each of the fine gold particles 13, 13, . . . of the sensor chip 10 is exposed to the side of the anodic oxidation alumina 12, which side is more outward than the one surface 12b of the anodic oxidation alumina 12. Therefore, the advantages over the cases, wherein fine metal particles are fixed to bottoms of deep fine holes, are capable of being obtained in that the antibody 31 is capable of being fixed to side surface areas, and the like, of each of the fine gold particles 13, 13, . . . Accordingly, the amount of the antibody 31 fixed to each of the fine gold particles 13, 13, . . . becomes large, and the change in refractive index at the peripheral area of each of the fine gold particles 13, 13, . . . , which change occurs due to the binding of the antibody 31 with the antigen 32, becomes large. As a result, a large change in sensor output signal is capable of being obtained. Therefore, with the sensor chip 10, an accurate analysis is capable of being performed.

Also, with the sensor chip 10, wherein each of the fine gold particles 13, 13, . . . , to which the antibody 31 is fixed, is located in the state described above, the advantages over the cases, wherein the fine metal particles are fixed to the bottoms of the deep fine holes, are capable of being obtained in that the antigen 32 need not diffuse within the fine hole to the position in the vicinity of the bottom of the fine hole and is capable of binding with the antibody 31. Therefore, the change in sensor output signal due to the binding of the antigen 32 with the antibody 31 is capable of being found quickly, and the efficiency with which the sample analysis is made is capable of being enhanced.

The characteristics illustrated in FIG. 4 are capable of being determined previously in accordance with experience or experiments.

In the embodiment described above, the measuring light 23, which is the white light and has been reflected from the sensor chip 10, is detected spectrophotometrically, and the resonance peak wavelength $\lambda_{LP}$ is thereby detected. Alternatively, monochromatic light may be employed as the measuring light, and the shift of the resonance peak wavelength $\lambda_{LP}$ or the change in light intensity accompanying the change in scattering and absorption of the measuring light 23 may be detected. In such cases, the occurrence of the binding of the antibody 31 with the antigen 32 is capable of being detected.

More specifically, examples of the combinations of the antibody 31 and the antigen 32 include a combination of biotin and streptoavidin, and the like. In such cases, in order for biotin to be fixed more firmly to the sensor chip 10, the surface of the anodic oxidation alumina 12 should preferably be modified with a self-assembled monolayer. The self-assembled monolayer of this type is described in detail in, for example, "Modeling Organic Surfaces with Self-Assembled Monolayers" by Colin D. Brain and George M. Whitesides, Angewandte Chemie International Edition in English, Vol. 28, No. 4, pp. 506-512, 1989.

Figure 5:
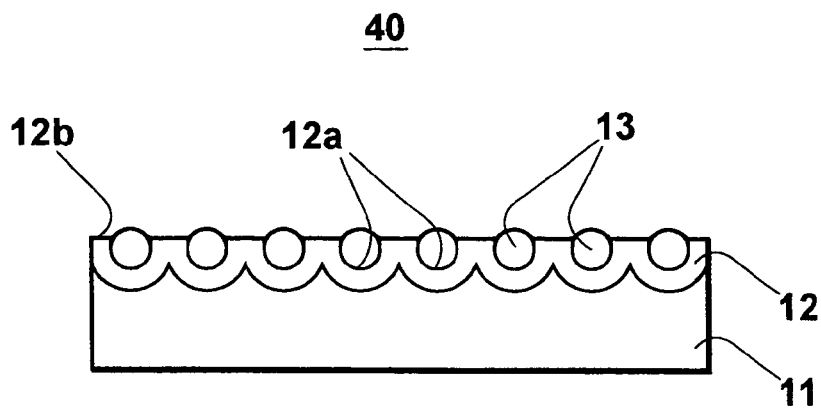
FIG. 5 is a schematic side view showing a different embodiment of the first sensor chip in accordance with the present invention.

A sensor chip 40, which is a different embodiment of the first sensor chip in accordance with the present invention, will be described hereinbelow with reference to FIG. 5. The sensor chip 40 is constituted basically in the same manner as that for the sensor chip 10 of FIG. 1, except that only a part of the surface of each of the fine gold particles 13, 13, . . . is exposed to the side of the anodic oxidation alumina 12, which side is more outward than the one surface 12b of the anodic oxidation alumina 12. In FIG. 5 (and those that follow), similar elements are numbered with the same reference numerals with respect to FIG. 1.

With the sensor chip 40 constituted in the manner described above, the part of the surface of each of the fine gold particles 13, 13, . . . is exposed to the side of the anodic oxidation alumina 12, which side is more outward than the one surface 12b of the anodic oxidation alumina 12. Therefore, as in the cases of the sensor chip 10 of FIG. 1, an accurate analysis is capable of being performed, and the efficiency with which the sample analysis is made is capable of being enhanced.

A sensor chip 50, which is a further different embodiment of the first sensor chip in accordance with the present invention, will be described here in below with reference to FIG. 6. The sensor chip 50 is constituted basically in the same manner as that for the sensor chip 10 of FIG. 1, except that the thickness of anodic oxidation alumina 121 of the sensor chip 50 is larger than the thickness of the anodic oxidation alumina 12 of the sensor chip 10, and the anodic oxidation alumina 12' having fine holes 12a', 12a' . . . is used in the state in which the anodic oxidation alumina 12' has been separated from the aluminum base plate 11 illustrated in FIG. 1. In this manner, the sensor chip 50 is constituted of the anodic oxidation alumina 12' acting as the unit body. Alternatively, the anodic oxidation alumina 12' may be secured to a different transparent member having a high rigidity, and a sensor chip comprising the anodic oxidation alumina 12' and the transparent member may thus be constituted.

Figure 7:
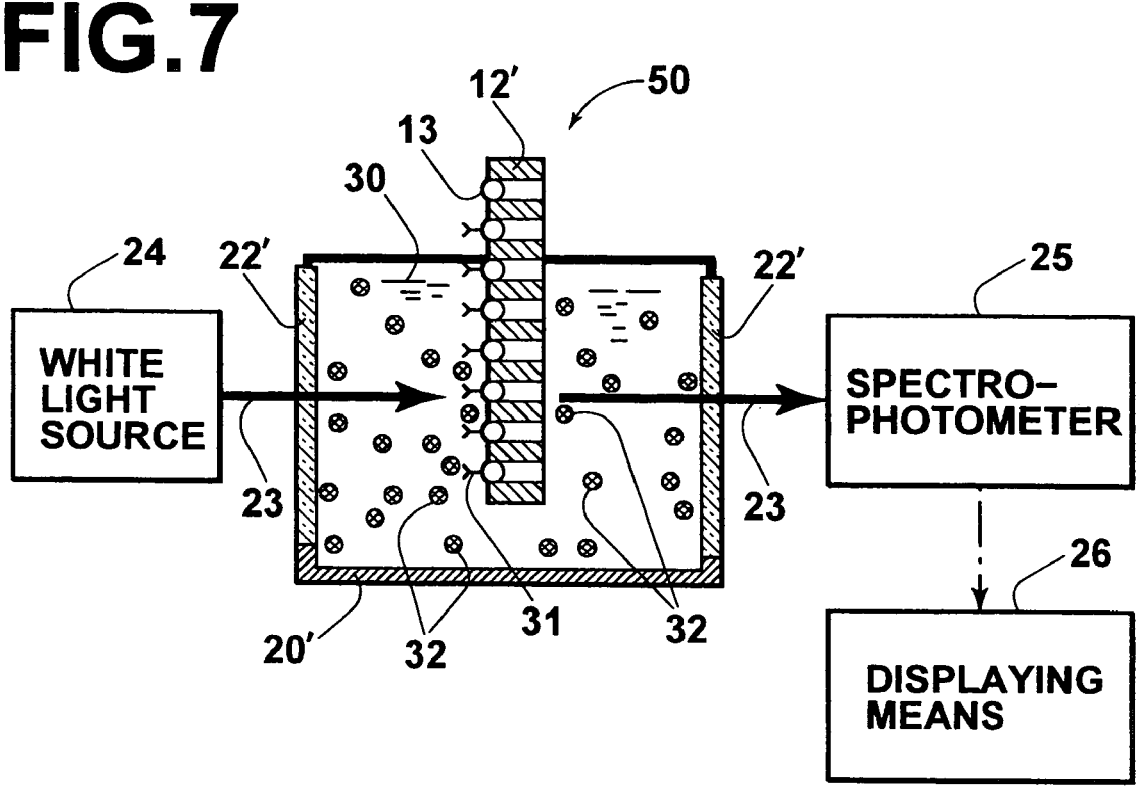
FIG. 7 is a schematic side view showing a different embodiment of the first sensor in accordance with the present invention.

The sensor chip 50 is used in order to constitute a biosensor illustrated in FIG. 7. The biosensor illustrated in FIG. 7 comprises the sensor chip 50, a vessel 20', the white light source 24, and the spectrophotometer 25. In this embodiment, the vessel 20' is provided with transparent windows 22', 22', which are formed at the side surfaces that stand facing each other. Also, the white light source 24 is located in an orientation such that the measuring light 23, which is the white light, enters through one of the transparent windows 22', 22' into the vessel 20'. Further, the spectrophotometer 25 is located in an orientation such that the spectrophotometer 25 receives the measuring light 23, which has passed through the vessel 20' and is radiated out from the other transparent window 22'. Furthermore, the sensor chip 50 is located at the position such that the sensor chip 50 enters into the optical path of the measuring light 23 within the vessel 20'.

In the embodiment of the sensor illustrated in FIG. 7, the sample liquid 30 to be analyzed is introduced into the vessel 20'. Also, the measuring light 23 traveling within the vessel 20' passes through the area of the fine gold particles 13, 13, . . . of the sensor chip 50, which particles are in contact with the sample liquid 30. The measuring light 23 having passed through the area of the fine gold particles 13, 13, . . . of the sensor chip 50 is detected by the spectrophotometer 25. Therefore, with this embodiment of the sensor, as in the cases of the sensor illustrated in FIG. 2, the occurrence of the binding of the antibody 31 and the antigen 32 is capable of being detected. Also, with this embodiment of the sensor chip 50, the part of the surface of each of the fine gold particles 13, 13, . . . is exposed to the side of the anodic oxidation alumina 12', which side is more outward than the one surface 12b of the anodic oxidation alumina 12'. Therefore, an accurate analysis is capable of being performed, and the efficiency with which the sample analysis is made is capable of being enhanced.

A sensor chip 60, which is a still further different embodiment of the first sensor chip in accordance with the present invention, will be described herein below with reference to FIG. 8. The sensor chip 60 is constituted basically in the same manner as that for the sensor chip 50 of FIG. 6, except that only a part of the surface of each of the fine gold particles 13, 13, . . . is exposed to the side of the anodic oxidation alumina 12', which side is more outward than the one surface 12b of the anodic oxidation alumina 12'.

The sensor chip 60 is capable of being used in order to constitute the transmission type of the sensor illustrated in FIG. 7. Also, with the sensor chip 60 constituted in the manner described above, the part of the surface of each of the fine gold particles 13, 13, . . . is exposed to the side of the anodic oxidation alumina 12', which side is more outward than the one surface 12b of the anodic oxidation alumina 12'. Therefore, as in the cases of the sensor chip 50 of FIG. 6, an accurate analysis is capable of being performed, and the efficiency with which the sample analysis is made is capable of being enhanced.

Figure 6:
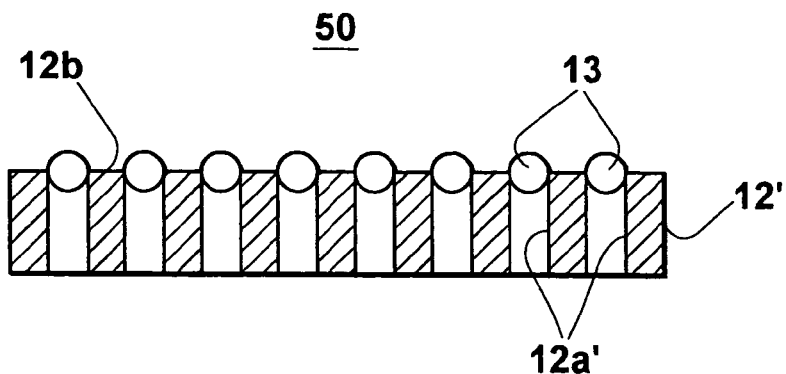
FIG. 6 is a schematic side view showing a further different embodiment of the first sensor chip in accordance with the present invention.
Figure 8:
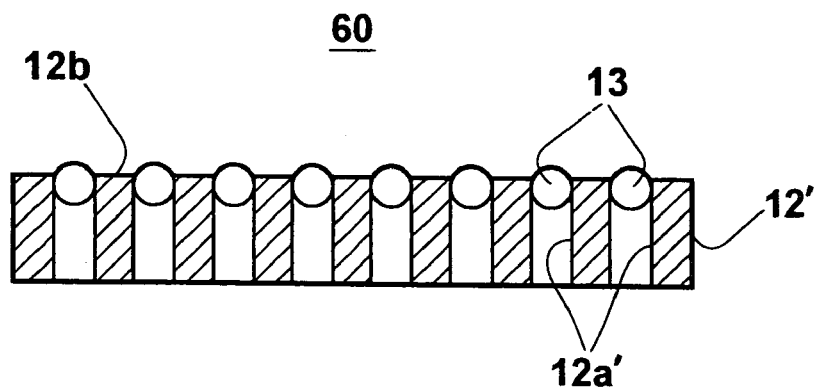
FIG. 8 is a schematic side view showing a still further different embodiment of the first sensor chip in accordance with the present invention.

In the process for producing the sensor chip 50 illustrated in FIG. 6 or the sensor chip 60 illustrated in FIG. 8, the aluminum base plate, on which the anodic oxidation alumina 12' has been formed, is removed from the anodic oxidation alumina 12'. For this purpose, for example, a technique, wherein the aluminum base plate is subjected to etching processing using a saturated $HgCl_2$ solution or an acid, such as sulfuric acid, may be employed. The aforesaid technique for the etching processing is described in, for example, Japanese Journal of Applied Physics, Vol. 37, pp. L1090-1092, 1998.

Figure 9:
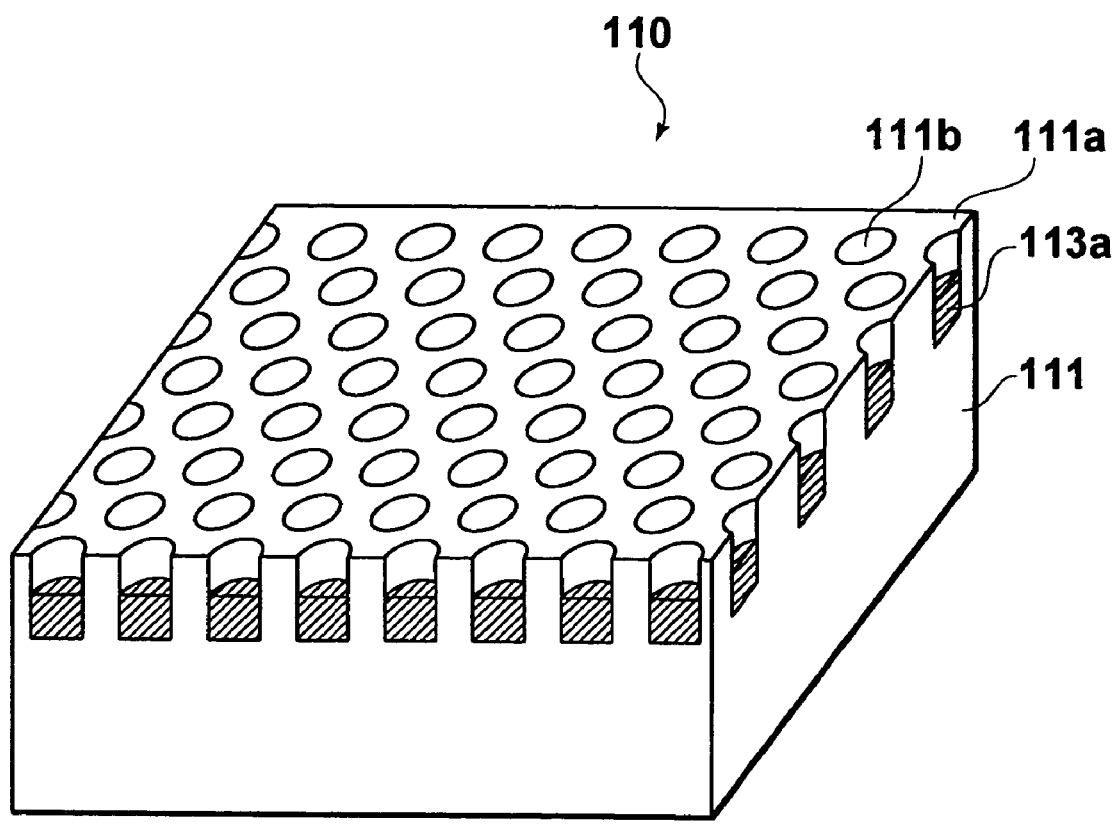
FIG. 9 is a perspective view showing an embodiment of the second sensor chip in accordance with the present invention.

An embodiment of the second sensor chip in accordance with the present invention will be described hereinbelow with reference to FIG. 9. FIG. 9 is a perspective view showing an embodiment of the second sensor chip in accordance with the present invention.

With reference to FIG. 9, a sensor chip 110 comprises a support member 111, which is constituted of a polystyrene. The support member 111 has a plurality of independent fine holes 111b, 111b, . . . , which extend in a direction approximately normal to a surface 111a of the support member 111. The sensor chip 110 also comprises independent fine gold (Au) particles 113a, 113a, . . . , each of which is supported within one of the fine holes 111b, 111b, . . . of the support member 111.

As illustrated in FIG. 9, the fine holes 111b, 111b, . . . are arrayed regularly. Each of the fine gold particles 113a, 113a, . . . loaded on the bottoms of the fine holes 111b, 111b, . . . has a diameter falling within the range of, for example, approximately several nanometers to approximately 200 nm. Also, the depth of each of the fine holes 111b, 111b, . . . may be set at an arbitrary value.

In this embodiment of the sensor chip 110, gold (Au) is employed as the fine gold particles 113a, 113a, . . . Gold constituting the fine gold particles 113a, 113a, . . . acting as the fine metal particles is a good electrical conductor and has good malleability and good ductility, and therefore the vacuum evaporation processing with gold is capable of being performed appropriately at comparatively low temperatures. Also, since gold has a high corrosion resistance, in cases where the sensor chip 110 provided with the fine gold particles 113a, 113a, . . . is utilized in a sensor, which will be described later, a sensor having stable characteristics is capable of being obtained. Further, the sensor chip 110 provided with the fine gold particles 113a, 113a, . . . is easy to process during the production and the use of the sensor.

In lieu of the fine gold particles 113a, 113a, . . . , fine metal particles constituted of silver or one of other metals may be employed. In particular, in cases where the fine metal particles are constituted of silver, the sensitivity of the sensor using the sensor chip is capable of being enhanced.

In this embodiment of the sensor chip 110, the diameter of each of the fine gold particles 1113a, 113a, . . . is set to be smaller than the depth of each of the fine holes 111b, 111b, . . . , and each of the fine gold particles 113a, 113a, . . . is supported at a part of the region within each of the fine holes 111b, 111b, . . . Alternatively, gold may be loaded over the entire area of each of the fine holes 111b, 111b, . . .

In this embodiment of the sensor chip 110, the support member 111 is constituted of the polystyrene having uniform density. Therefore, with sensor chip 110, the occurrence of optical noise is capable of being suppressed, and the signal-to-noise ratio is capable of being enhanced. As a result, measurement with a high sensitivity is capable of being performed.

In this embodiment of the sensor chip 110, the support member 111 is constituted of the polystyrene acting as the transparent dielectric material. In lieu of the polystyrene, a high-molecular weight resin, such as a polymethylmethacrylate (PMMA), may be employed as the transparent dielectric material for constituting the support member 111.

An embodiment of the process for producing the second sensor chip in accordance with the present invention will be described hereinbelow. FIGS. 10A to 10E are sectional views showing how the second sensor chip in accordance with the present invention is produced.

Figure 10A:
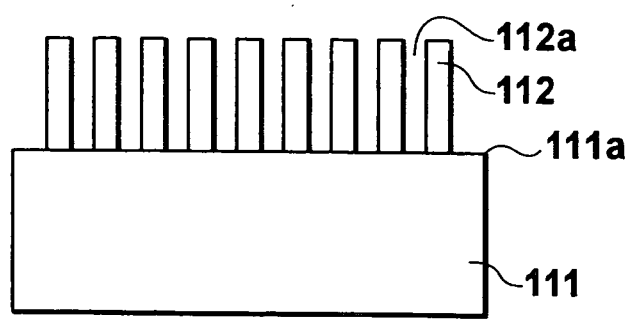
FIGS. 10A to 10E are sectional views showing how the second sensor chip in accordance with the present invention is produced.

Specifically, firstly, as illustrated in FIG. 10A, an anodic oxidation alumina film 112 is formed on a polystyrene base plate 111.

The anodic oxidation alumina film 112 may be formed on the polystyrene base plate 111 in the manner described below. The anodic oxidation alumina film 112 may be formed with one of various techniques. Basically, a technique is employed wherein, when aluminum having been formed on the polystyrene base plate 111 is subjected to anodic oxidation in an acidic electrolyte, the formation of an oxide film and the dissolution of the oxide film having been formed are allowed to progress simultaneously. With the technique described above, with the dissolving effect of the acid, fine pits (fine holes) occur at random in the surface of the oxide film, which has been formed on the aluminum at the initial stage of the anodic oxidation. Also, as the anodic oxidation progresses, certain pits among the pits described above grow preferentially, and a plurality of pits are thus arrayed at approximately equal intervals in the surface of the oxide film. An area of the oxide film, at which a pit has been formed, is exerted to an electric field, which is stronger than the electric field applied to the other areas of the oxide film. Therefore, the dissolution of the area of the oxide film, at which the pit has been formed, is promoted. As a result, in the oxide layer on anode, as the oxide layer grows, the fine holes are formed by selective dissolution, and a wall area, which is not dissolved and remains in the pattern surrounding each of the fine holes, is formed.

As illustrated in FIG. 10A, in the anodic oxidation alumina film 112 obtained in the manner described above, a plurality of first fine holes 112a, 112a, . . . are formed in a regularly arrayed pattern on the surface 111a of the polystyrene base plate 111. Each of the first fine holes 112a, 112a, . . . constitutes a circular cylinder-shaped space, which extends in the direction approximately normal to the layer surface of the anodic oxidation alumina film 112 having been formed and has an approximately identical cross-sectional shape.

The anodic oxidation alumina film 112 may be formed with the processing, wherein an aluminum film is formed on the surface 111a of the polystyrene base plate 111 in the manner described above and is then subjected to the anodic oxidation. Alternatively, the anodic oxidation alumina film 112 may be formed previously and may then be laminated with the polystyrene base plate 111.

Figure 10B:
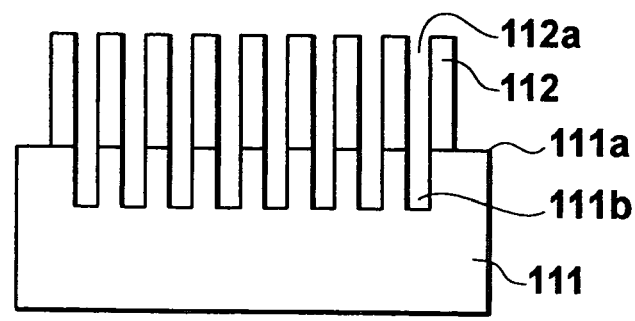

Thereafter, as illustrated in FIG. 10B, the polystyrene base plate 111 is subjected to etching processing, in which the anodic oxidation alumina film 112 having been formed on the surface 111a of the polystyrene base plate 111 is utilized as a mask. In this manner, a plurality of the second fine holes 111b, 111b, . . . , each of which corresponds to one of the first fine holes 112a, 112a, . . . , are formed in the surface 111a of the polystyrene base plate 111. The etching processing may be performed by use of an etchant, such as oxygen or $CF_4$.

Figure 10C:
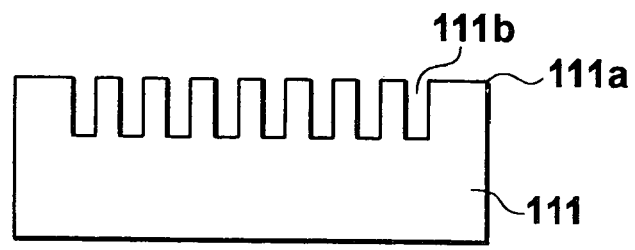

Thereafter, as illustrated in FIG. 10C, the anodic oxidation alumina film 112 is removed from the surface 111a of the polystyrene base plate 111.

Figure 10D:
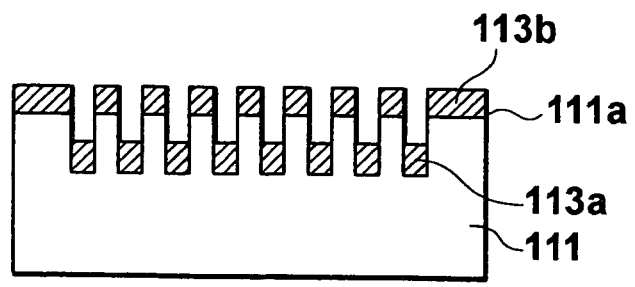

Thereafter, as illustrated in FIG. 10D, a gold depositing operation, such as a vacuum evaporation operation with gold or a sputtering operation with gold, is performed on the polystyrene base plate 111 having the surface 111a, in which the second fine holes 111b, 111b, . . . have been formed. The gold depositing operation is performed from the side of the surface 111a of the polystyrene base plate 111. With the gold depositing operation, each of the fine gold particles 113a, 113a, . . . is formed within one of the second fine holes 111b, 111b, . . . Also, a gold deposit layer 113b is formed on the surface 111a of the polystyrene base plate 111.

Figure 10E:
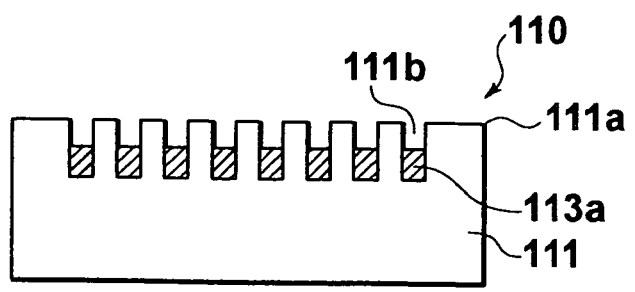

Thereafter, as illustrated in FIG. 10E, only the metal deposit layer 113b having formed on the surface 111a of the polystyrene base plate 111 is removed from the surface 111a of the polystyrene base plate 111. In this manner, each of independent fine gold particles 113a, 113a, . . . is capable of being supported with in one of the second fine holes 111b, 111b, . . . The metal deposit layer 113b having been formed on the surface 111a of the polystyrene base plate 111 is capable of being easily scraped off by use of an applicator. Alternatively, the metal deposit layer 113b may be removed with a polishing operation using a file, or the like.

As for techniques for regulating the fine holes, techniques for forming start points of fine hole formation are disclosed in, for example, Japanese Unexamined Patent Publication Nos. 2001-9800 and 2001-138300. Specifically, the start points of fine hole formation are formed at desired positions on the site of a workpiece containing aluminum as a principal constituent. Thereafter, the workpiece is subjected to the anodic oxidation processing. In this manner, the fine holes are capable of being formed at the desired positions. Therefore, the array of the fine holes of a nano-structure, the intervals of the fine holes, the positions of the fine holes, the orientation of the fine holes, and the like, are capable of being regulated. As the technique for forming the start points of fine hole formation, the conditions at the time of the irradiation of the converged ion beam, such as the quantity of irradiation of the converged ion beam, the diameter of the converged ion beam, and the irradiation energy, may be adjusted. In this manner, the recess shapes and compositions of the fine hole start points are capable of being regulated. Therefore, the fine hole diameters of the finally formed nanoholes are capable of being regulated.

Further, as a technique for forming the array of the fine holes at a particularly high density, for example, a technique wherein oxalic acid is used may be employed. Specifically, oxalic acid may be utilized as the electrolyte for the anodic oxidation, and the anodic oxidation processing may be performed at a predetermined voltage of approximately 40V. In such cases, the fine holes are capable of being formed in a regularly arrayed pattern and at a high density. The regularity of the array of the fine holes progresses with the passage of time of anodic oxidation. Therefore, in cases where the anodic oxidation processing is performed for a long period of time, the fine holes are capable of being formed in an approximately ideal array pattern. Accordingly, the array of the fine holes formed in the anodic oxidation alumina film takes a markedly high regularity which is exceptional for structures formed naturally.

As described above, with the embodiment of the process for producing the second sensor chip in accordance with the present invention, the polystyrene base plate 111 is subjected to the etching processing, in which the anodic oxidation alumina film 112 having the regularly arrayed first fine holes 112a, 112a, . . . is utilized as the mask. In this manner, the plurality of the second fine holes 111b, 111b, . . . are formed in the surface 111a of the polystyrene base plate 111. Therefore, the fine holes 111b, 111b, . . . are capable of being arrayed at a high density. Also, the fine gold particles 113a, 113a, . . . are capable of being formed such that the fine gold particles 113a, 113a, . . . have uniform size. Further, the sizes of the fine gold particles 113a, 113a, . . . are capable of being set at an arbitrary value. Accordingly, various sensor chips appropriate for various purposes of use are capable of being obtained.

Furthermore, with the aforesaid embodiment of the process for producing the second sensor chip in accordance with the present invention, a mask having been obtained from fine patterning with a lithographic technique, or the like, or an electron beam drawing technique, which requires a high cost and has a low productivity, need not be utilized, and a sensor chip having the fine metal particles arrayed at a high density is capable of being obtained easily.

Figure 11:
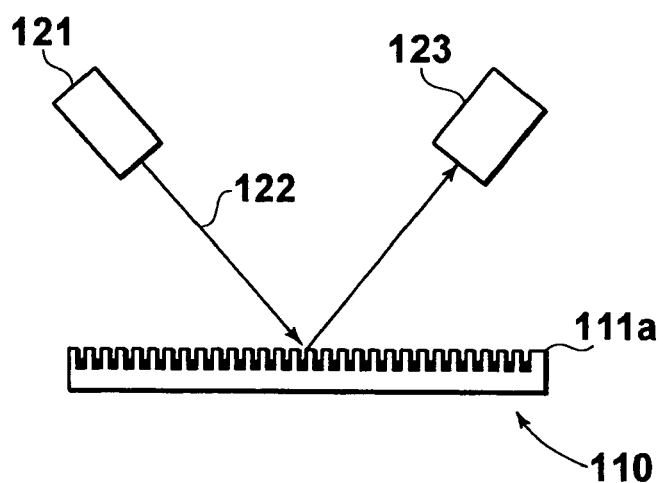
FIG. 11 is a schematic view showing an embodiment of the second sensor in accordance with the present invention, which is constituted as a reflection type of sensor.

An embodiment of the second sensor in accordance with the present invention, wherein the second sensor chip in accordance with the present invention is used, will be described hereinbelow. FIG. 11 is a schematic view showing an embodiment of the second sensor in accordance with the present invention, which is constituted as a reflection type of sensor.

As illustrated in FIG. 11, the embodiment of the second sensor in accordance with the present invention comprises the sensor chip 110 in accordance with the present invention. The sensor also comprises a light source 121 for irradiating measuring light 122 from the side of openings of the fine holes 111b, 111b, . . . to the sensor chip 110, such that the measuring light 122 impinges at an oblique angle upon an area of the fine gold particles 113a, 113a, . . . The sensor further comprises a polychromator 123, which acts as the photo detecting means for measuring the intensity of the light having been reflected from the sensor chip.

The size of each of the fine gold particles 113a, 113a, . . . having been supported within the fine holes 111b, 111b, . . . , which size is taken in the diameter direction of the fine hole, and the size of each of the fine gold particles 113a, 113a, . . . , which size is taken in the depth direction of the fine hole, are approximately identical with each other. Therefore, the electric field direction of the incident light may be parallel with the plane of the sheet of FIG. 11 or may be normal to the plane of the sheet of FIG. 11. In cases where each of the fine gold particles having been supported within the second fine holes 111b, 111b, . . . takes a rod-like shape, in which the length of the fine gold particle is larger than the diameter of the fine gold particle, the electric field direction of the measuring light should preferably be parallel with the plane of the sheet of FIG. 11.

The measuring light 122 having been produced by the light source 121 impinges upon the area of the fine gold particles 113a, 113a, . . . of the sensor chip 110 and is reflected from the area of the fine gold particles 113a, 113a, . . . of the sensor chip 110. The intensity of the measuring light 122 having thus been reflected from the area of the fine gold particles 113a, 113a, . . . is detected by the photo detecting means, which may be constituted of the polychromator 123, or the like.

Figure 12:
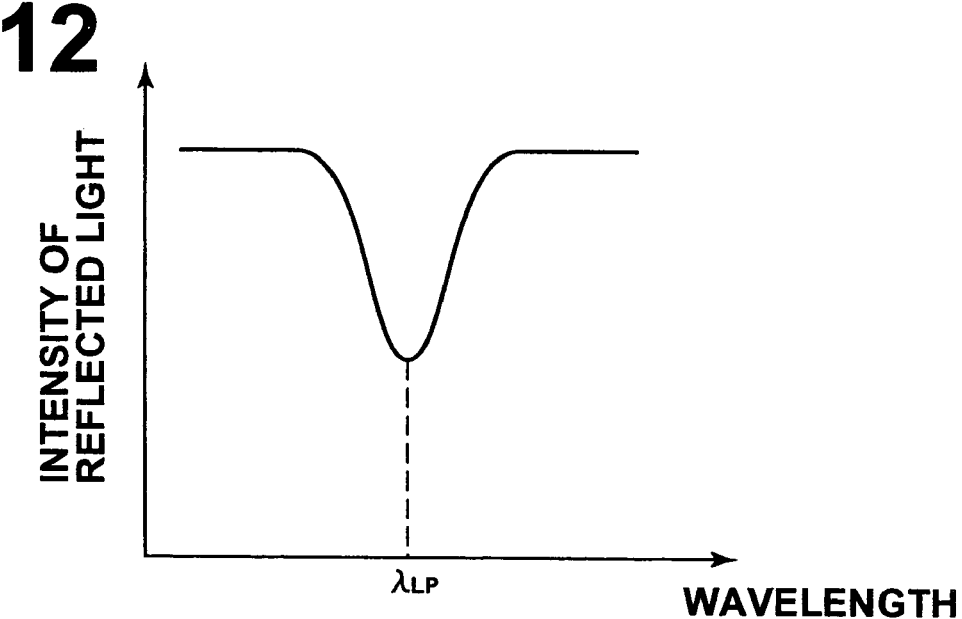
FIG. 12 is a graph showing the relationship between wavelengths of reflected light and intensity of the reflected light at the time of localized plasmon resonance.

FIG. 12 is a graph showing the relationship between wavelengths of reflected light and intensity of the reflected light at the time of localized plasmon resonance.

Specifically, in cases where the measuring light 122 is irradiated to the area of the fine gold particles 113a, 113a, . . . of the sensor chip 110, as for a light component having a specific wavelength $\lambda_{LP}$, the scattering and the absorption of the measuring light 122 increase specifically due to the localized plasmon resonance. Therefore, as for the light component having the specific wavelength $\lambda_{LP}$, the intensity of the reflected light becomes markedly low. Also, the wavelength (the resonance peak wavelength) $\lambda_{LP}$, at which the localized plasmon resonance occurs, and the extent of the scattering and the absorption of the measuring light 122 depend upon the refractive index of the sample, which is present at the peripheral areas of the fine gold particles 113a, 113a, . . . More specifically, as the refractive index of the sample, which is present at the peripheral areas of the fine gold particles 113a, 113a, . . . , becomes large, the resonance peak wavelength $\lambda_{LP}$ shifts to the long wavelength side. Therefore, in cases where the resonance peak wavelength $\lambda_{LP}$ is detected, the refractive index of the sample, which is present in the vicinity of the fine gold particles 113a, 113a, . . . , the physical properties of the sample corresponding to the refractive index, and the like, are capable of being measured. The refractive index of the sample, which is present in the vicinity of the fine gold particles 113a, 113a, . . . , and the physical properties of the sample corresponding to the refractive index, are capable of being calculated by use of a signal processing section.

Figure 13:
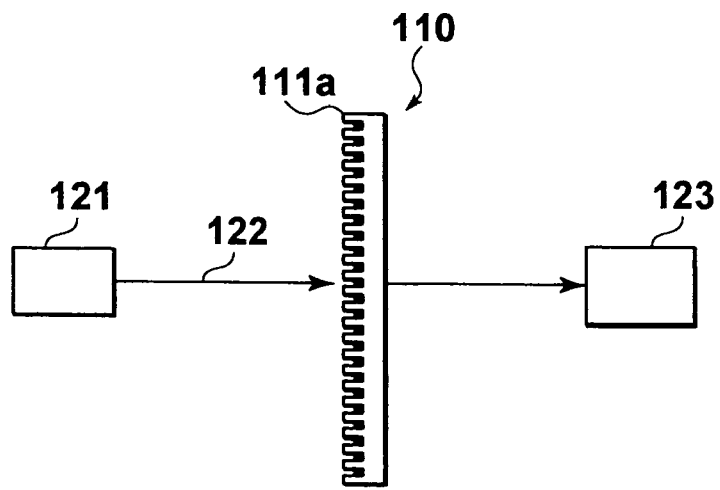
FIG. 13 is a schematic view showing a different embodiment of the second sensor in accordance with the present invention, which is constituted as a transmission type of sensor.

In this embodiment of the second sensor in accordance with the present invention, the intensity of the reflected light is measured. Alternatively, as illustrated in FIG. 13, the second sensor in accordance with the present invention may be constituted as a transmission type of sensor. In the different embodiment of the second sensor illustrated in FIG. 13, the measuring light 122 having been produced by the light source 121 is irradiated from the side of the surface 111a of the sensor chip 110, which surface is provided with the fine holes 111b, 111b, . . . The measuring light 122 is irradiated from the direction normal to the surface 111a of the sensor chip 110. Also, the intensity of the measuring light 122 having passed through the sensor chip 110 is detected by the polychromator 123 acting the photo detecting means. As another alternative, the measuring light 122 having been produced by the light source 121 may be irradiated from a direction other than the direction normal to the surface 111a of the sensor chip 110, which surface is provided with the fine holes 111b, 111b, . . .

Also, white light may be employed as the measuring light 122, and the measuring light 122 having been reflected from the sensor chip 110 or having passed through the sensor chip 110, may be detected spectrophotometrically. In this manner, the resonance peak wavelength $\lambda_{LP}$ may be detected. Alternatively, monochromatic light may be employed as the measuring light 122, and the shift of the resonance peak wavelength $\lambda_{LP}$ or the change in light intensity accompanying the change in scattering and absorption of the measuring light 122 may be detected. In such cases, the refractive index of the sample, the physical properties of the sample, and the like, are capable of being measured.

Figure 14:
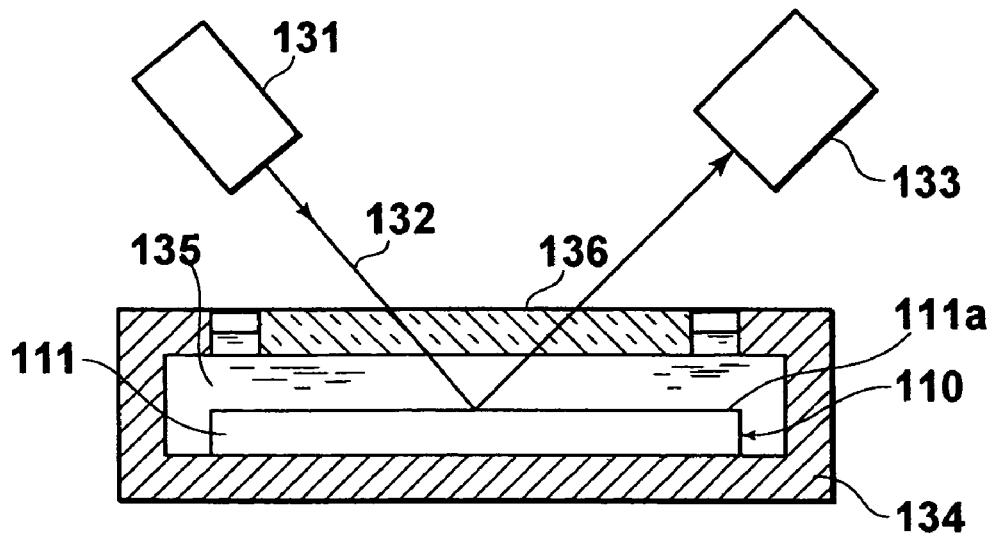
FIG. 14 is a schematic view showing a further different embodiment of the second sensor in accordance with the present invention, which is constituted as a biosensor.

A further different embodiment of the second sensor in accordance with the present invention, wherein the second sensor chip in accordance with the present invention is used, will be described hereinbelow. FIG. 14 is a schematic view showing a further different embodiment of the second sensor in accordance with the present invention, which is constituted as a biosensor.

As illustrated in FIG. 14, the biosensor comprises the sensor chip 110 in accordance with the present invention. The biosensor also comprises a vessel 134 having a transparent window 136, which is formed at the top surface of the vessel 134. The sensor chip 110 is secured to the inside bottom surface of the vessel 134. The biosensor further comprises a light source 131 for irradiating white light (measuring light) 132 to the sensor chip 110 secured to the inside bottom surface of the vessel 134. The biosensor still further comprises a polychromator 133 for spectrophotometrically detecting the measuring light 132, which has been reflected from the sensor chip 110. The sensor chip 110 is located in the vessel 134 in an orientation such that the surface 111a of the sensor chip 110, which surface is provided with the fine holes 111b, 111b, ..., stands facing up.

Figure 15:
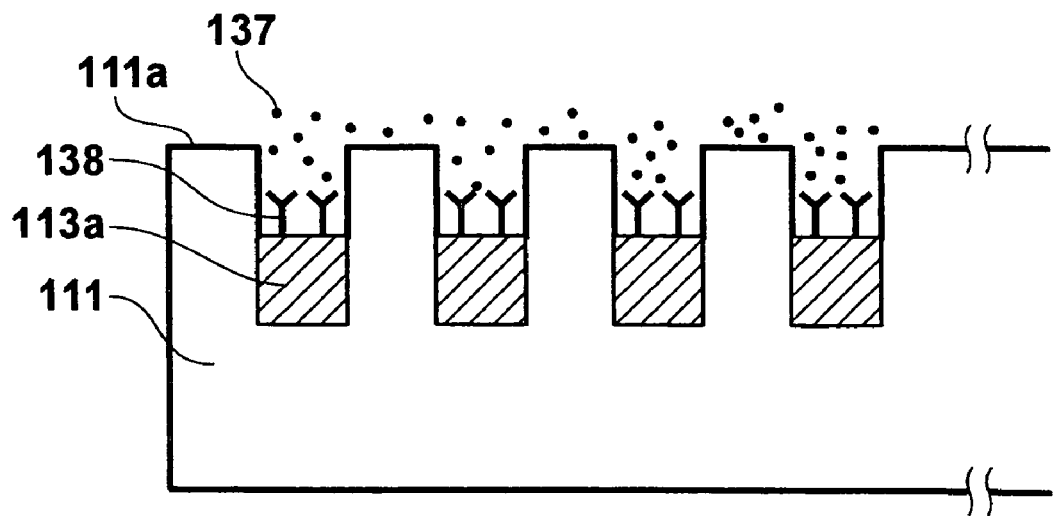
FIG. 15 is a partial sectional view showing a state at a surface of the second sensor chip in accordance with the present invention, which is used as the biosensor.

As illustrated in FIG. 15, by way of example, an antibody 138 (indicated by the Y-shaped mark in FIG. 15) has been fixed to the surface of each of the fine gold particles 113a, 113a, ... of the sensor chip 110. Also, a sample liquid 135 to be analyzed is introduced into the vessel 134 such that the sample liquid 135 comes into contact with the sensor chip 110. The sample liquid 135 contains a specific antigen 137, which is capable of undergoing specific binding with the antibody 138.

In cases where the antigen 137 is bound to the antibody 138, the refractive index at the peripheral areas of the fine gold particles 113a, 113a, ... of the sensor chip 110 changes. As a result, the absorption and scattering spectral characteristics of the measuring light 132 detected by the polychromator 133 change. By way of example, as described above with reference to FIG. 4, the change in absorption and scattering spectral characteristics of the measuring light 132 detected by the polychromator 133 appears as the shift of the resonance peak wavelength. Therefore, the change in resonance peak wavelength may be detected by the polychromator 133. In this manner, from the change in resonance peak wavelength, it is possible to find whether the binding of the antibody 138 with the antigen 137 has or has not occurred, i.e. whether the antigen 137 is or is not present in the sample liquid 135.

In this embodiment of the biosensor in accordance with the present invention, the sensor chip 110, in which the transparent dielectric material for supporting the fine gold particles 113a, 113a, ... is constituted of the polystyrene, is employed. Therefore, non-specific adsorption of the antigen 137 to the polystyrene base plate 111 does not occur. Accordingly, the occurrence of optical noise is capable of being suppressed, and measurement with a high sensitivity is capable of being performed.

Embodiments of the fine structure body in accordance with the present invention will be described hereinbelow.

Figure 16:
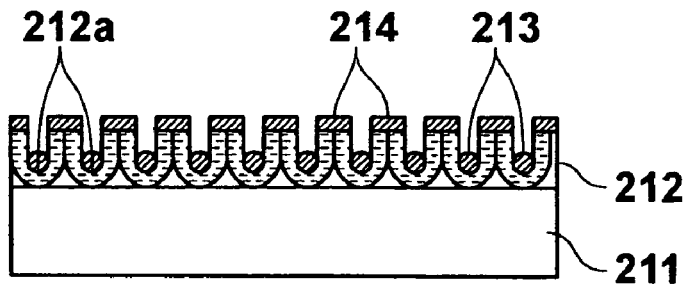
FIG. 16 is a schematic side view showing an embodiment of the fine structure body in accordance with the present invention.

FIG. 16 is a schematic side view showing a fine structure body 210, which is an embodiment of the fine structure body in accordance with the present invention. As illustrated in FIG. 16, the fine structure body 210 comprises an aluminum base plate 211. The fine structure body 210 also comprises anodic oxidation alumina 212, which is formed on the aluminum base plate 211 and acts as the layer-shaped base body.

The anodic oxidation alumina 212 has a plurality of fine holes 212a, 212a, ..., which are formed in one surface (the upper surface in FIG. 16). The fine structure body 210 further comprises fine gold (Au) particles 213, 213, ..., each of which is loaded in one of the fine holes 212a, 212a, ... The fine structure body 210 still further comprises a thin gold film 214 formed on areas of the one surface of the anodic oxidation alumina 212, which areas are located around each of the fine holes 212a, 212a, ... of the anodic oxidation alumina 212.

In this embodiment of the fine structure body 210, by way of example, each of the fine holes 212a, 212a, ... has a depth of at most approximately 200 nm. Each of the fine gold particles 213, 213, ... loaded on the bottoms of the fine holes 212a, 212a, ... has a diameter falling within the range of, for example, approximately several nanometers to approximately 100 nm. Also, the distance between each of the fine gold particles 213, 213, ... and the thin gold film 214, i.e. the distance between the top end of each of the fine gold particles 213, 213, ... and the bottom end of the thin gold film 214, is set to be equal to at most the diameter of each of the fine gold particles 213, 213, ...

Figure 17A:
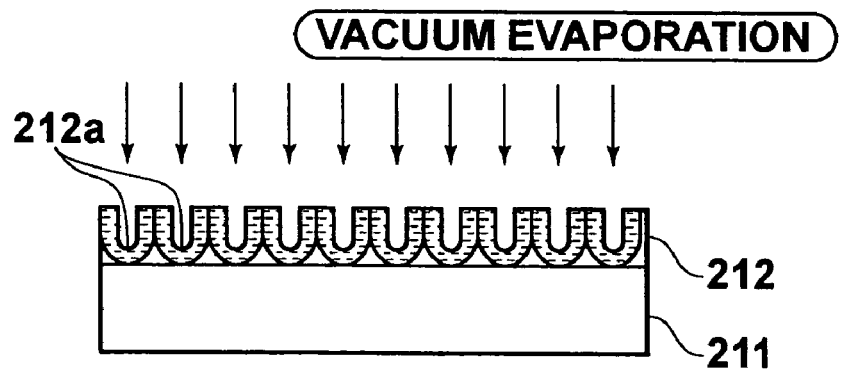
FIGS. 17A and 17B are schematic views showing an example of how the fine structure body of FIG. 16 is produced.
Figure 17B:
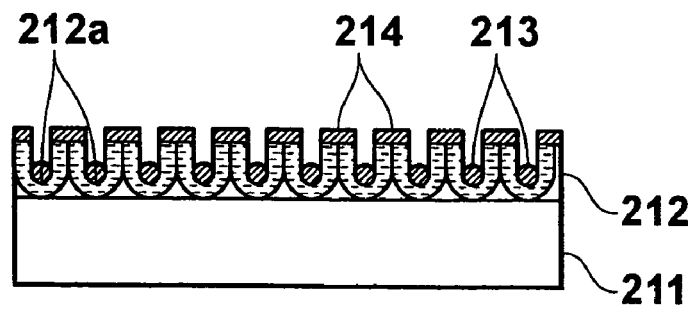

By way of example, the fine structure body 210 having the constitution described above may be produced in the manner described below. FIGS. 17A and 17B are schematic views showing an example of how the fine structure body 210 of FIG. 16 is produced. Specifically, firstly, as illustrated in FIG. 17A, the aluminum base plate 211 having the surface, on which the film of the anodic oxidation alumina 212 has been formed, is prepared. Thereafter, vacuum evaporation processing with gold is performed on the anodic oxidation alumina 212. The vacuum evaporation processing with gold is performed from the side of the one surface of the anodic oxidation alumina 212, in which surface the fine holes 212a, 212a, ... have been formed. With the vacuum evaporation processing, as illustrated in FIG. 17B, each of the fine gold particles 213, 213, ... is loaded in one of the fine holes 212a, 212a, ... of the anodic oxidation alumina 212, and the thin gold film 214 is formed on the aforesaid one surface of the anodic oxidation alumina 212. This embodiment of the fine structure body 210 is thus obtained.

Figure 18A:
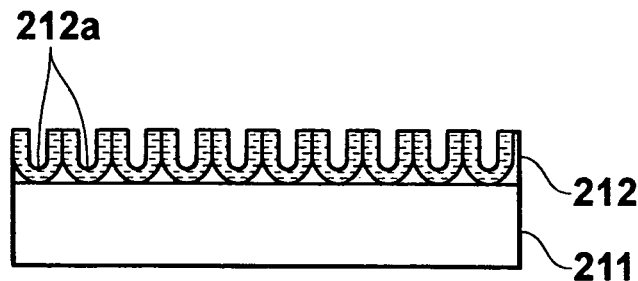
FIGS. 18A, 18B, and 18C are schematic views showing a different example of how the fine structure body of FIG. 16 is produced.
Figure 18B:
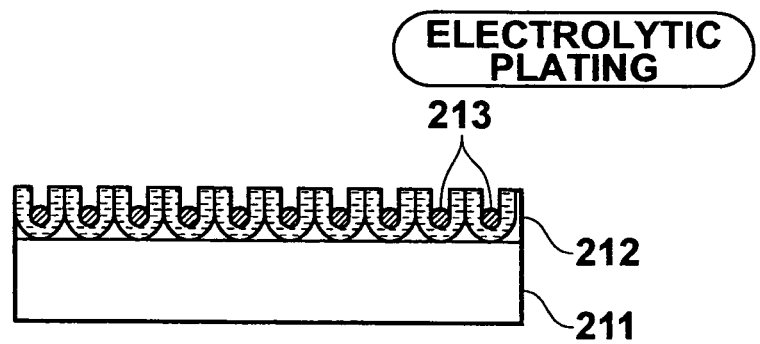
Figure 18C:
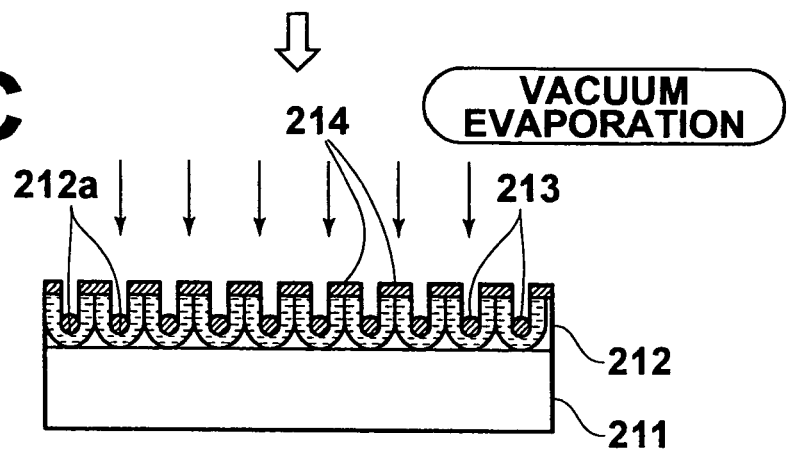

Alternatively, this embodiment of the fine structure body 210 may be produced in the manner described below. FIGS. 18A, 18B, and 18C are schematic views showing a different example of how the fine structure body 210 of FIG. 16 is produced. Specifically, firstly, as illustrated in FIG. 18A, the aluminum base plate 211 having the surface, on which the film of the anodic oxidation alumina 212 has been formed, is prepared. Thereafter, electrolytic plating processing with gold is performed on the anodic oxidation alumina 212. The electrolytic plating processing with gold is performed from the side of the one surface of the anodic oxidation alumina 212, in which surface the fine holes 212a, 212a, ... have been formed. With the electrolytic plating processing, as illustrated in FIG. 18B, each of the fine gold particles 213, 213, ... is loaded in one of the fine holes 212a, 212a, ... of the anodic oxidation alumina 212. In cases where the conditions for the electrolytic plating processing are adjusted appropriately, the electrolytic plating processing is capable of being performed such that gold plating is not effected on the surface area of the anodic oxidation alumina 212, and each of the fine gold particles 213, 213, ... is loaded only in one of the fine holes 212a, 212a, ... of the anodic oxidation alumina 212.

Thereafter, the vacuum evaporation processing with gold is performed on the anodic oxidation alumina 212. The vacuum evaporation processing with gold is performed from the side of the one surface of the anodic oxidation alumina 212, in which surface the fine holes 212a, 212a, ... have been formed. With the vacuum evaporation processing, as illustrated in FIG. 18C, the thin gold film 214 is formed on the aforesaid one surface of the anodic oxidation alumina 212. This embodiment of the fine structure body 210 may thus be obtained. In cases where the conditions for the vacuum evaporation processing are adjusted appropriately, the vacuum evaporation processing is capable of being performed such that the gold is not deposited within each of the fine gold particles 213, 213, . . . , and only the thin gold film 214 is formed on the aforesaid one surface of the anodic oxidation alumina 212.

In lieu of the fine gold particles 213, 213, . . . and the thin gold film 214, fine metal particles and a thin metal film of a different metal, e.g. silver, maybe formed. However, from the view point described below, gold is particularly preferable as the material for the formation of the fine structure body in accordance with the present invention. Specifically, gold has good malleability and good ductility, and therefore the vacuum evaporation processing with gold is capable of being performed appropriately at comparatively low temperatures. Also, since gold has a high corrosion resistance, in cases where the fine structure body 210 provided with the fine gold particles 213, 213, . . . and the thin gold film 214 is utilized in a sensor, which will be described later, a sensor having stable characteristics is capable of being obtained. Further, the fine structure body 210 provided with the fine gold particles 213, 213, . . . and the thin gold film 214 is easy to process during the production and the use of the sensor.

The layer-shaped anodic oxidation alumina 212 may be formed on the aluminum base plate 211 in the manner described below. The layer-shaped anodic oxidation alumina 212 may be formed with one of various techniques. Basically, a technique is employed wherein, when the aluminum base plate 211 is subjected to anodic oxidation in an acidic electrolyte, the formation of an oxide film and the dissolution of the oxide film having been formed are allowed to progress simultaneously. With the technique described above, with the dissolving effect of the acid, fine pits (fine holes) occur at random in the surface of the oxide film, which has been formed on the aluminum base plate 211 at the initial stage of the anodic oxidation. Also, as the anodic oxidation progresses, certain pits among the pits described above grow preferentially, and a plurality of pits are thus arrayed at approximately equal intervals in the surface of the oxide film. An area of the oxide film, at which a pit has been formed, is exerted to an electric field, which is stronger than the electric field applied to the other areas of the oxide film. Therefore, the dissolution of the area of the oxide film, at which the pit has been formed, is promoted. As a result, in the layer-shaped anodic oxidation alumina 212, as the layer-shaped anodic oxidation alumina 212 grows, the fine holes 212a, 212a, . . . are formed by selective dissolution, and an area, which is not dissolved and remains in the pattern surrounding each of the fine holes 212a, 212a, . . . , is formed.

In the anodic oxidation alumina 212 obtained in the manner described above, the plurality of the fine holes 212a, 212a, . . . are formed in the regularly arrayed pattern. Each of the fine holes 212a, 212a, . . . constitutes a circular cylinder-shaped space, which extends in the direction approximately normal to the surface of the anodic oxidation alumina 212. Also, the circular cylinder-shaped space constituted by each of the fine holes 212a, 212a, . . . has an approximately identical cross-sectional shape and a closed bottom.

Techniques for regulating the positions, at which the fine holes are formed, are disclosed in, for example, Japanese Unexamined Patent Publication Nos. 2001-9800 and 2001-138300. With the disclosed techniques for regulating the positions, at which the fine holes are formed, for example, a converged ion beam is irradiated to aluminum, and dissolution start points are thereby formed at desired positions on the aluminum. Thereafter, the anodic oxidation processing is performed in the manner described above. In this manner, the fine holes 212a, 212a, . . . are capable of being formed at the desired positions. Also, by the adjustment of the conditions at the time of the irradiation of the converged ion beam, such as the quantity of irradiation of the converged ion beam, the diameter of the converged ion beam, and the irradiation energy, the recess shapes and compositions of the dissolution start points are capable of being altered. Therefore, the diameters of the finally formed fine holes 212a, 212a, . . . are capable of being regulated freely.

Further, as a technique for forming the array of the fine holes 212a, 212a, . . . at a particularly high density, for example, a technique wherein oxalic acid is used may be employed. Specifically, oxalic acid may be utilized as the electrolyte for the anodic oxidation, and the anodic oxidation processing may be performed at a predetermined voltage of approximately 40V. In such cases, the fine holes 212a, 212a, . . . are capable of being formed in a regularly arrayed pattern and at a high density. The regularity of the array of the fine holes 212a, 212a, . . . progresses with the passage of time of anodic oxidation. Therefore, in cases where the anodic oxidation processing is performed for a long period of time, the fine holes 212a, 212a, . . . , which are located at a high regularity and at a high density, are capable of being formed.

In the manner described above, the diameters, the intervals, and the depths of the fine holes 212a, 212a, . . . are capable of being regulated comparatively freely. Therefore, the fine gold particles 213, 213, . . . and the thin gold film 214 are capable of being formed with arbitrary uniform size and are capable of being located regularly. As a result, in cases where the fine structure body 210 is used in the sensor, which will be described later, the sensitivity of the sensor is capable of being enhanced and kept stable.

Figure 19:
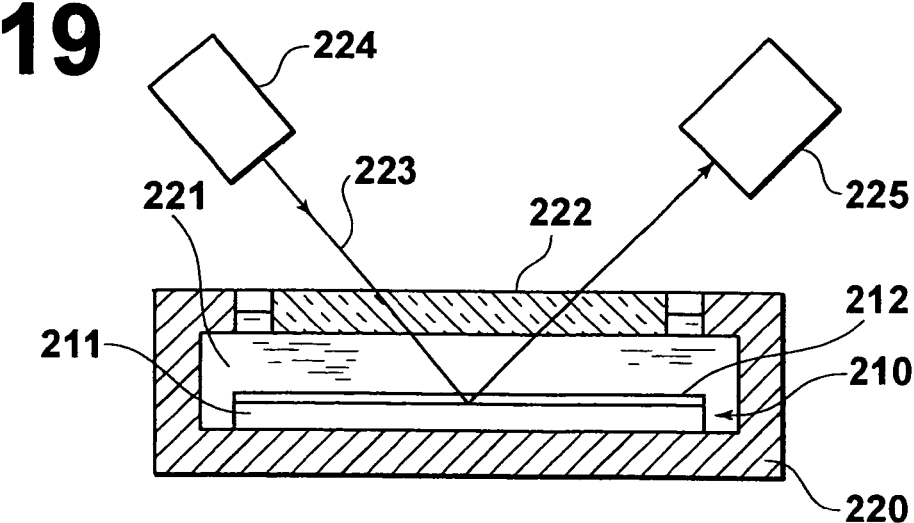
FIG. 19 is a schematic side view showing an embodiment of the third sensor in accordance with the present invention.

An embodiment of the third sensor in accordance with the present invention will be described hereinbelow. FIG. 19 is a side view showing an embodiment of the third sensor in accordance with the present invention, wherein the fine structure body 210 described above is used. As illustrated in FIG. 19, the sensor comprises a vessel 220 having a transparent window 222, which is formed at the top surface of the vessel 220. The fine structure body 210 is secured to the inside bottom surface of the vessel 220. The sensor also comprises a white light source 224 for irradiating measuring light 223 obliquely toward the fine structure body 210 secured to the inside bottom surface of the vessel 220. The sensor further comprises a spectrophotometer 225 for spectrophotometrically detecting the measuring light 223, which has been reflected from the fine structure body 210.

The fine structure body 210 is located within the vessel 220 such that the one surface of the anodic oxidation alumina 212, which surface is provided with the fine gold particles 213, 213, . . . and the thin gold film 214, stands facing up. Also, a sample liquid 221 to be analyzed is introduced into the vessel 220 such that the sample liquid 221 comes into contact with the anodic oxidation alumina 212.

The measuring light 223, which is the white light, is irradiated through the transparent window 222 of the vessel 220 to the fine structure body 210, which has been located within the vessel 220 in the manner described above. In such cases, the measuring light 223 is reflected from the irradiated area of the fine gold particles 213, 213, . . . and the thin gold film 214 (illustrated in FIG. 16). The measuring light 223 having thus been reflected from the irradiated area of the fine gold particles 213, 213, . . . and the thin gold film 214 is spectrophotometrically detected by the spectrophotometer 225. Also, in such cases, the measuring light 223 passes through the area of the anodic oxidation alumina 212, at which area the fine gold particles 213, 213, . . . and the thin gold film 214 are present. The measuring light 223 having passed through the aforesaid area of the anodic oxidation alumina 212 is reflected upwardly from the aluminum base plate 211. The measuring light 223 having thus been reflected upwardly from the aluminum base plate 211 is also spectrophotometrically detected by the spectrophotometer 225.

Figure 20:
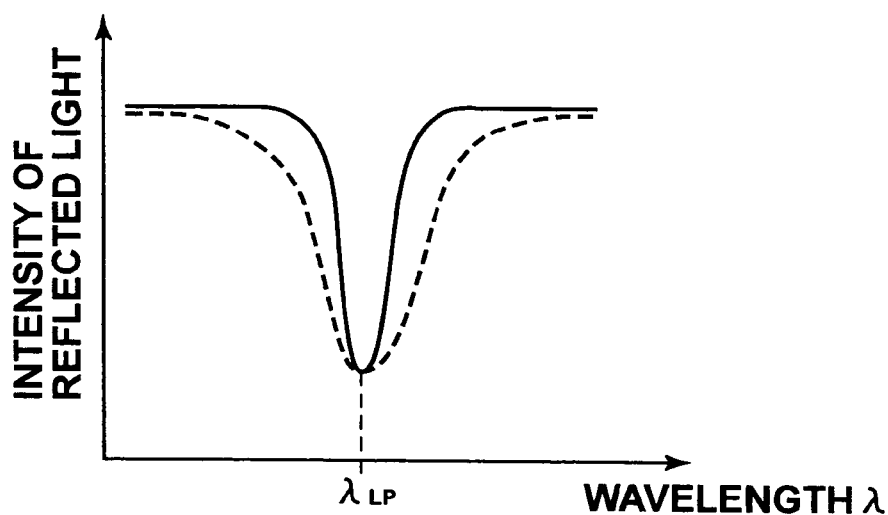
FIG. 20 is a graph showing spectral intensity characteristics of measuring light detected with the sensor shown in FIG. 19.

The reflected light, which is thus detected, has the spectral intensity characteristics basically identical with the spectral intensity characteristics indicated by the solid line in FIG. 20. Specifically, in cases where the measuring light 223 is irradiated to the area of the fine gold particles 213, 213, . . . of the anodic oxidation alumina 212, as for a light component having a specific wavelength $\lambda_{LP}$, the scattering and the absorption of the measuring light increase specifically due to the localized plasmon resonance. Therefore, as for the light component having the specific wavelength $\lambda_{LP}$, the intensity of the reflected light becomes markedly low.

Also, the wavelength (the resonance peak wavelength) $\lambda_{LP}$, at which the localized plasmon resonance occurs, and the extent of the scattering and the absorption of the measuring light 223 depend upon the refractive index of the sample liquid 221, which is present at the peripheral areas of the fine gold particles 213, 213, . . . More specifically, as the refractive index of the sample liquid 221, which is present at the peripheral areas of the fine gold particles 213, 213, . . . , becomes large, the resonance peak wavelength $\lambda_{LP}$ shifts to the long wavelength side. Therefore, in cases where the measuring light 223 is irradiated to the area of the anodic oxidation alumina 212 having been located in the vessel 220 containing the sample liquid 221, and, for example, the resonance peak wavelength $\lambda_{LP}$ is detected at this time, the refractive index of the sample liquid 221, which is present in the vicinity of the fine gold particles 213, 213, . . . , the physical properties of the sample liquid 221 corresponding to the refractive index, and the like, are capable of being measured.

Also, in the fine structure body 210 used in the sensor described above, the thin gold film 214 is located at the spacing, which is approximately equal to at most the diameter of each of the fine gold particles 213, 213, . . . , from each of the fine gold particles 213, 213, . . . Therefore, near field light, which occurs when the measuring light 223 is irradiated to an area of the fine gold particles 213, 213, . . . , interacts with the thin gold film 214, and an absorption spectrum due to electric multipoles occurs with the measuring light 223. Further, the surface plasmon resonance is excited by the interaction between the measuring light 223, which is totally reflected within the transparent anodic oxidation alumina 212, and the thin gold film 214.

Therefore, with the sensor described above, the measuring light absorption and scattering spectral characteristics alter sharply due to the synergistic effects of the localized plasmon resonance, the electric multipoles, and the surface plasmon resonance. Specifically, in cases where only the localized plasmon resonance occurring with only the fine gold particles 213, 213, . . . is utilized, the absorption and scattering spectral characteristics of the measuring light 223 become identical with the absorption and scattering spectral characteristics indicated by the broken line in FIG. 20. However, with this embodiment of the sensor in accordance with the present invention, the absorption and scattering spectral characteristics of the measuring light 223 become identical with the absorption and scattering spectral characteristics indicated by the solid line in FIG. 20. The absorption and scattering spectral characteristics indicated by the solid line in FIG. 20 are such that the intensity of the reflected light changes sharply with respect to a slight change in wavelength, i.e. a slight change in refractive index of the sample liquid 221. Therefore, with the sensor described above, the refractive index of the sample liquid 221, the physical properties of the sample liquid 221 corresponding to the refractive index, and the like, are capable of being measured markedly accurately.

The characteristics illustrated in FIG. 20 are capable of being determined previously in accordance with experience or experiments.

In the embodiment of the sensor described above, the measuring light 223, which is the white light and has been reflected from the fine structure body 210, is detected spectrophotometrically, and the resonance peak wavelength $\lambda_{LP}$ is thereby detected. Alternatively, monochromatic light may be employed as the measuring light, and the shift of the resonance peak wavelength $\lambda_{LP}$ or the change in light intensity accompanying the change in scattering and absorption of the measuring light 223 may be detected. In such cases, the refractive index of the sample liquid 221, the physical properties of the sample liquid 221 corresponding to the refractive index, and the like, are capable of being measured.

Figure 21:
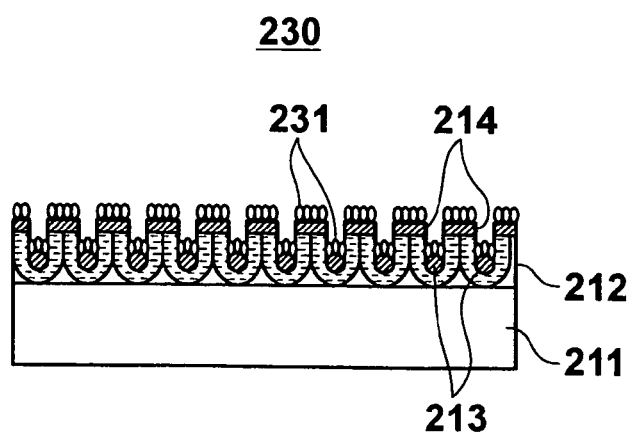
FIG. 21 is a schematic side view showing a different embodiment of the fine structure body in accordance with the present invention.

A fine structure body 230, which is a different embodiment of the fine structure body in accordance with the present invention, will be described here in below with reference to FIG. 21. The fine structure body 230 is constituted basically in the same manner as that for the fine structure body 210 shown in FIG. 16, except that an antibody 231 is fixed previously onto the fine gold particles 213, 213, . . . and the thin gold film 214.

Figure 22:
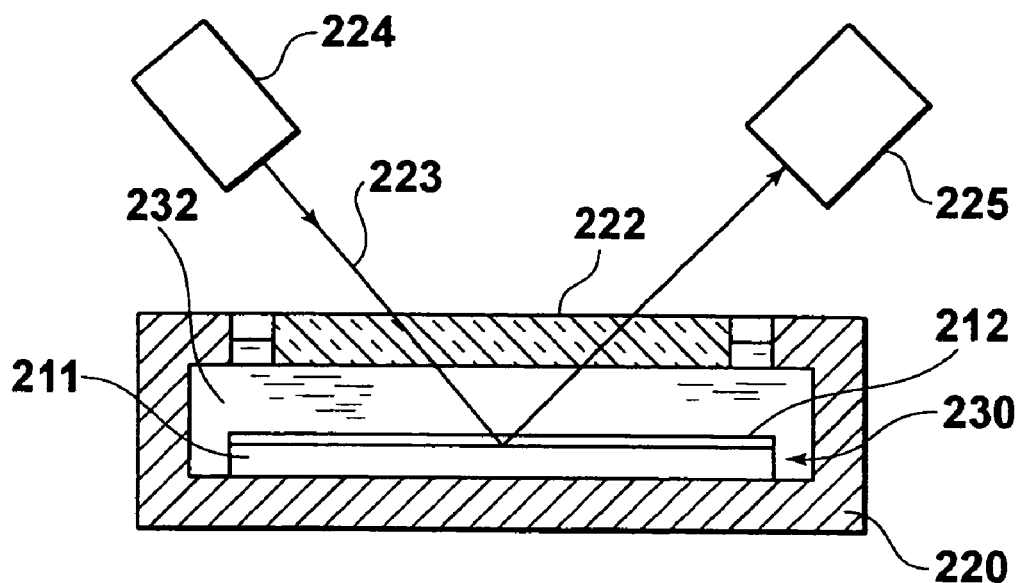
FIG. 22 is a schematic side view showing a different embodiment of the third sensor in accordance with the present invention.
Figure 23:
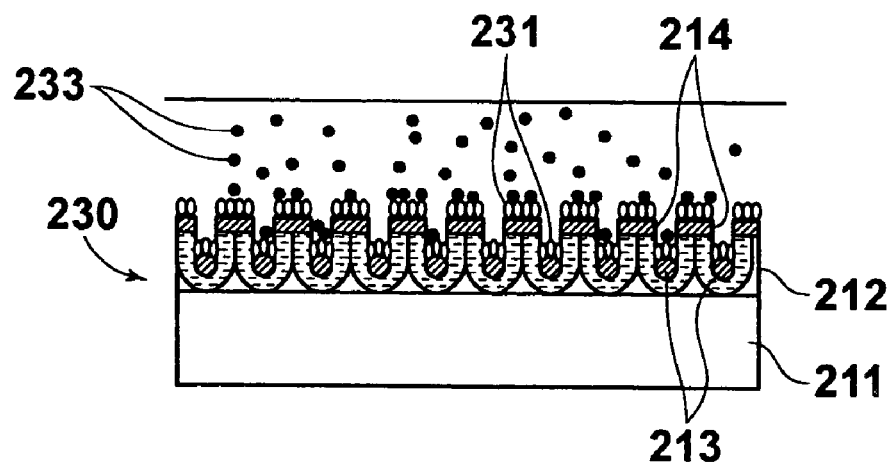
FIG. 23 is a schematic side view showing a state of the fine structure body of FIG. 21 at the time of sample analysis.

The fine structure body 230 is capable of being used in order to constitute a biosensor illustrated in FIG. 22. The biosensor illustrated in FIG. 22 is constituted basically in the same manner as that for the biosensor illustrated in FIG. 19, except that the fine structure body 230 is used in lieu of the fine structure body 210. In this embodiment of the biosensor, a sample liquid 232 to be analyzed is introduced into the vessel 220 such that the sample liquid 232 comes into contact with the anodic oxidation alumina 212 of the fine structure body 230. In this case, the sample liquid 232 contains a specific antigen 233, which is capable of undergoing specific binding with the antibody 231. In such cases, as illustrated in FIG. 23, the antigen 233 is bound to the antibody 231 of the fine structure body 230.

In cases where the antigen 233 is bound to the antibody 231, the refractive index at the peripheral areas of the fine gold particles 213, 213, . . . and the thin gold film 214 of the fine structure body 230 changes. As a result, the absorption and scattering spectral characteristics of the measuring light 223 detected by the spectrophotometer 225 change. By way of example, as described above with reference to FIG. 4, the change in absorption and scattering spectral characteristics of the measuring light 223 detected by the spectrophotometer 225 appears as the shift of the resonance peak wavelength. Therefore, the change in resonance peak wavelength may be detected by the spectrophotometer 225. In this manner, from the change in resonance peak wavelength, it is possible to find whether the binding of the antibody 231 with the antigen 233 has or has not occurred, i.e. whether the antigen 233 is or is not present in the sample liquid 232.

With this embodiment of the biosensor, the near field light, which occurs when the measuring light 223 is irradiated to an area of the fine gold particles 213, 213, . . . , interacts with the thin gold film 214, and an absorption spectrum due to electric multipoles occurs with the measuring light 223. Further, the surface plasmon resonance is excited by the interaction between the measuring light 223, which is totally reflected within the transparent anodic oxidation alumina 212, and the thin gold film 214. Therefore, the measuring light absorption and scattering spectral characteristics alter sufficiently sharply due to the synergistic effects of the localized plasmon resonance, the electric multipoles, and the surface plasmon resonance. Accordingly, a slight binding of the antigen 233 with the antibody 231 is capable of being detected accurately.

More specifically, examples of the combinations of the antibody 231 and the antigen 233 include a combination of biotin and streptoavidin, and the like. In such cases, in order for biotin to be fixed more firmly to the fine structure body 230, the surface of the anodic oxidation alumina 212 should preferably be modified with a self-assembled monolayer. The self-assembled monolayer of this type is described in detail in, for example, "Modeling Organic Surfaces with Self-Assembled Monolayers" by Colin D. Brain and George M. Whitesides, Angewandte Chemie International Edition in English, Vol. 28, No. 4, pp. 506-512, 1989.

A further different embodiment of the fine structure body in accordance with the present invention and a further different embodiment of the third sensor in accordance with the present invention will be described hereinbelow with reference to FIG. 24. In this embodiment, a fine structure body 240 comprises an anodic oxidation alumina 212', to which the fine gold particles 213, 213, . . . and the thin gold film 214 have been fixed. The anodic oxidation alumina 212' takes on the form having been separated from the aluminum base plate 211 of the fine structure body 230 shown in FIG. 21. In this manner, the fine structure body 240 is constituted of the anodic oxidation alumina 212' acting as the unit body. Alternatively, the anodic oxidation alumina 212' may be secured to a different transparent member having a high rigidity, and a fine structure body comprising the anodic oxidation alumina 212' and the transparent member may thus be constituted.

The sensor, in which the fine structure body 240 is used, comprises the fine structure body 240, a vessel 220', the white light source 224, and the spectrophotometer 225. In this embodiment, the vessel 220' is provided with transparent windows 222', 222', which are formed at the side surfaces that stand facing each other. Also, the white light source 224 is located in an orientation such that the measuring light 223, which is the white light, enters through one of the transparent windows 222', 222' into the vessel 220'. Further, the spectrophotometer 225 is located in an orientation such that the spectrophotometer 225 receives the measuring light 223, which has passed through the vessel 220' and is radiated out from the other transparent window 222'. Furthermore, the fine structure body 240 is located at the position such that the fine structure body 240 enters into the optical path of the measuring light 223 within the vessel 220'.

In the embodiment of the sensor illustrated in FIG. 24, the sample liquid 232 to be analyzed is introduced into the vessel 220'. Also, the measuring light 223 traveling within the vessel 220' passes through the area of the fine gold particles 213, 213, . . . and the thin gold film 214 of the fine structure body 240, which area is in contact with the sample liquid 232. The measuring light 223 having passed through the area of the fine gold particles 213, 213, . . . and the thin gold film 214 of the fine structure body 240 is detected by the spectrophotometer 225. Therefore, with this embodiment of the sensor, as in the cases of the sensor illustrated in FIG. 22, the occurrence of the binding of the antibody 231 (indicated by the Y-shaped mark in FIG. 24) and the antigen 233 is capable of being detected.

A still further different embodiment of the fine structure body in accordance with the present invention and a still further different embodiment of the third sensor in accordance with the present invention will be described hereinbelow with reference to FIG. 25. In this embodiment, a fine structure body 250 is constituted basically in the same manner as that for the fine structure body 240 shown in FIG. 24, except that the antibody 231 has previously be fixed also to the fine gold particles 213, 213, . . . , which are exposed from aback surface of the anodic oxidation alumina 212' (i.e., the right end face of the anodic oxidation alumina 212' in FIG. 25) to the exterior of the anodic oxidation alumina 212'.

Also, the sensor illustrated in FIG. 25 is constituted basically in the same manner as that for the sensor illustrated in FIG. 24, except that the fine structure body 250 is used in lieu of the fine structure body 240. With the sensor illustrated in FIG. 25, as in the cases of the sensor illustrated in FIG. 24, the binding of the antibody 231 with the antigen 233 is capable of being detected accurately.

Figure 26:
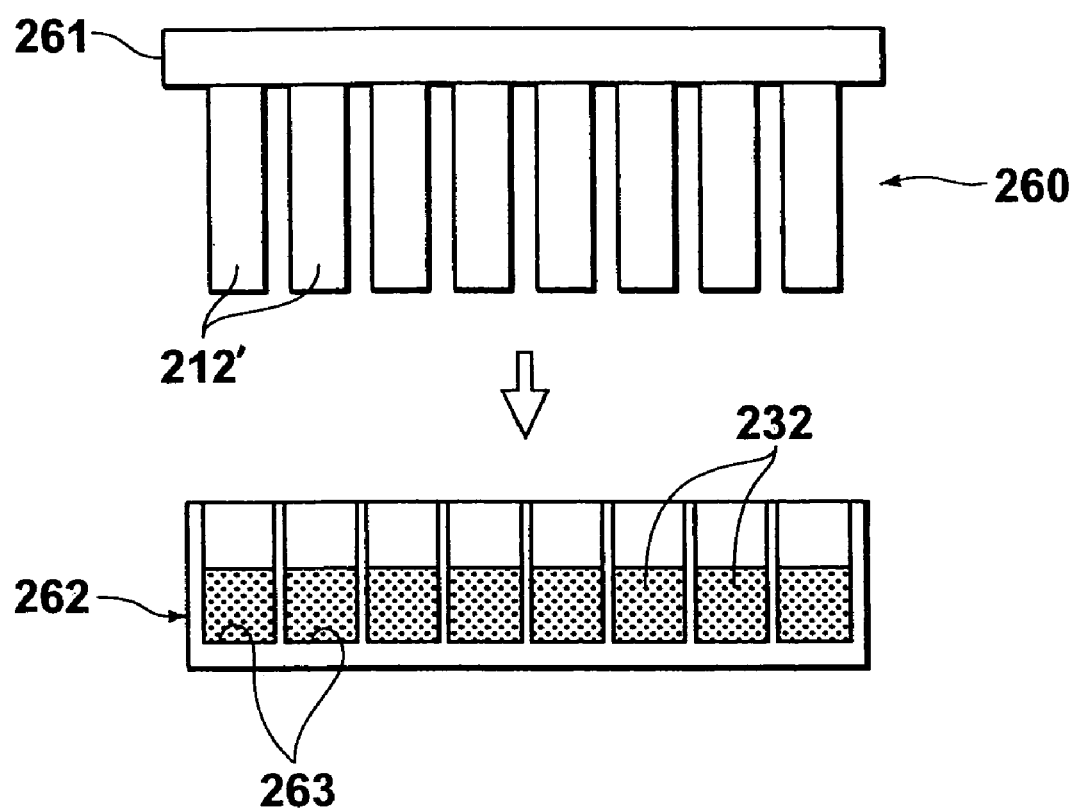
FIG. 26 is a schematic view showing an even further different embodiment of the fine structure body in accordance with the present invention.

An even further different embodiment of the fine structure body in accordance with the present invention will be described hereinbelow with reference to FIG. 26. In this embodiment, a fine structure body 260 comprises a support member 261. The fine structure body 260 also comprises a plurality of anodic oxidation alumina bodies 212', 212', . . . , which are supported together with one another by the support member 261. The anodic oxidation alumina bodies 212', 212', . . . are arrayed in a row at predetermined intervals. By way of example, each of the anodic oxidation alumina bodies 212', 212', . . . may be constituted in the same manner as that for the anodic oxidation alumina 212' constituting the fine structure body 240 shown in FIG. 24. Though not shown in FIG. 26, as in the cases of the fine structure body 240, each of the anodic oxidation alumina bodies 212', 212', . . . is provided with the fine gold particles 213, 213, . . . and the thin gold film 214. Also, the antibody 231 has been fixed to the fine gold particles 213, 213, . . . and the thin gold film 214.

In this embodiment of the fine structure body 260, by way of example, eight anodic oxidation alumina bodies 212', 212', . . . are supported together with each other by the support member 261. The array pitch of the anodic oxidation alumina bodies 212', 212', . . . is set to be identical with the array pitch of wells 263, 263, . . . of a micro-titer plate 262. By way of example, the micro-titer plate 262 may have 8×12 (=96) holes. Therefore, each of the eight anodic oxidation alumina bodies 212', 212', . . . of the fine structure body 260 is capable of being dipped in one of the eight wells 263, 263, . . . of the micro-titer plate 262, which are arrayed in one direction. In this manner, different sample liquids 232, 232, . . . , which have been accommodated respectively in the wells 263, 263, . . . , are capable of being simultaneously supplied to the anodic oxidation alumina bodies 212', 212', . . . of the fine structure body 260.

After each of the different sample liquids 232, 232, . . . has thus been supplied to one of the anodic oxidation alumina bodies 212', 212', . . . of the fine structure body 260, the fine structure body 260 is capable of being used in order to detect the binding of the antibody 231 with the antigen 233 by use of, for example, the white light source 224 and the spectrophotometer 225 as illustrated in FIG. 24 or FIG. 25. In such cases, the vessel 220' for containing the sample liquid as illustrated in FIG. 24 or FIG. 25 becomes unnecessary.

Also, in cases where eight sets, each of which comprises the combination of the white light source 224 and the spectrophotometer 225, are utilized simultaneously, the operations for irradiating the measuring light and the operations for detecting the intensity of the transmitted light are capable of being performed simultaneously with respect to the eight anodic oxidation alumina bodies 212', 212', . . . , to which the different sample liquids 232, 232, . . . have been supplied. Alternatively, only one set, which comprises the combination of the white light source 224 and the spectrophotometer 225, may be utilized, and the fine structure body 260 may be moved with respect to the one set of the combination of the white light source 224 and the spectrophotometer 225. In this manner, the eight anodic oxidation alumina bodies 212', 212', . . . may be successively sent to the one set of the combination of the white light source 224 and the spectrophotometer 225 at short time intervals. In such cases, the operations for irradiating the measuring light and the operations for detecting the intensity of the transmitted light are capable of being performed efficiently with respect to the eight anodic oxidation alumina bodies 212', 212', . . .

As described above, with this embodiment of the fine structure body 260, the operations for supplying the sample liquids, the operations for irradiating the measuring light, and the operations for detecting the intensity of the transmitted light are capable of being performed efficiently. Therefore, the analyses and the measurements with respect a plurality of samples are capable of being performed quickly.

What is claimed is:

1. A sensor using a fine structure body,
   wherein the fine structure body comprises:
   i) a layer-shaped base body, which has a plurality of fine holes formed in one surface,
   ii) fine metal particles, each of which is loaded in one of the fine holes of the base body, and
   iii) a thin metal film formed on areas of the one surface of the layer-shaped base body, which areas are located around each of the fine holes of the layer-shaped base body, such that the thin metal film is located at a spacing from each of the fine metal particles;
   wherein the layer-shaped base body comprises dielectric material or semiconductor material,
   wherein the sensor comprises:
   i) means for irradiating measuring light to an area of the fine metal particles and the thin metal film of the fine structure body, and
   ii) photo detecting means for detecting intensity of the measuring light, which has passed through the area of the fine metal particles and the thin metal film, or has been reflected from the area of the fine metal particles and the thin metal film.

2. A sensor as defined in claim 1 wherein the photo detecting means spectrophotometrically detects the intensity of the measuring light, which has passed through the area of the fine metal particles and the thin metal film, or has been reflected from the area of the fine metal particles and the thin metal film.

* * * * *